(12) United States Patent
Rabiner et al.

(10) Patent No.: US 7,794,414 B2
(45) Date of Patent: Sep. 14, 2010

(54) APPARATUS AND METHOD FOR AN ULTRASONIC MEDICAL DEVICE OPERATING IN TORSIONAL AND TRANSVERSE MODES

(75) Inventors: Robert A. Rabiner, North Reading, MA (US); Bradley A. Hare, Chelmsford, MA (US); Rebecca I. Marciante, North Reading, MA (US); Mark J. Varady, Andover, MA (US)

(73) Assignee: Emigrant Bank, N.A., New York, NY (US)

( * ) Notice: Subject to any disclaimer, the term of this patent is extended or adjusted under 35 U.S.C. 154(b) by 1691 days.

(21) Appl. No.: 10/774,898

(22) Filed: Feb. 9, 2004

(65) Prior Publication Data

US 2005/0187513 A1 Aug. 25, 2005

(51) Int. Cl.
*A61H 1/00* (2006.01)
(52) U.S. Cl. ............................................ 601/2; 604/22
(58) Field of Classification Search .................... 604/22; 606/1, 159, 169, 171; 601/2–4
See application file for complete search history.

(56) References Cited

U.S. PATENT DOCUMENTS

| | | | |
|---|---|---|---|
| 168,975 A | 10/1875 | Farmer | |
| 323,762 A | 8/1885 | White | |
| 404,319 A | 5/1889 | Taylor | |
| 414,090 A | 10/1889 | Taylor | |
| 1,045,326 A | 11/1912 | Ruflin | |
| 1,239,451 A | 9/1917 | Belz | |
| 1,779,478 A | 10/1930 | Leech | |
| 1,861,769 A | 6/1932 | Wappler | |
| 2,199,602 A | 5/1940 | Wright | |
| 2,242,120 A | 5/1941 | Gardiner | |

(Continued)

FOREIGN PATENT DOCUMENTS

CA 2251096 8/1998

(Continued)

OTHER PUBLICATIONS

International Search Report based on PCT/US04/03694 dated Aug. 27, 2004.

(Continued)

*Primary Examiner*—Brian Casler
*Assistant Examiner*—Peter Luong
(74) *Attorney, Agent, or Firm*—Greenberg Traurig, LLP; David J. Dykeman; Danielle T. Abramson

(57) ABSTRACT

The present invention provides an apparatus and a method for an ultrasonic medical device operating in a torsional mode and a transverse mode. An ultrasonic probe of the ultrasonic medical device is placed in communication with a biological material. An ultrasonic energy source is activated to produce an electrical signal that drives a transducer to produce a torsional vibration of the ultrasonic probe. The torsional vibration produces a component of force in a transverse direction relative to a longitudinal axis of the ultrasonic probe, thereby exciting a transverse vibration along the longitudinal axis causing the ultrasonic probe to undergo both a torsional vibration and a transverse vibration. The torsional vibration and the transverse vibration cause cavitation in a medium surrounding the ultrasonic probe to ablate the biological material.

69 Claims, 10 Drawing Sheets

U.S. PATENT DOCUMENTS

| | | |
|---|---|---|
| 2,270,922 A | 1/1942 | Bechmann et al. |
| 2,321,358 A | 6/1943 | Bokovoy |
| 2,514,080 A | 7/1950 | Mason |
| 2,742,076 A | 4/1956 | Klein |
| 2,838,695 A | 6/1958 | Thurston .................... 310/361 |
| 2,843,176 A | 6/1958 | Franck |
| 2,917,691 A | 12/1959 | De Prisco et al. |
| 2,990,616 A | 7/1961 | Balamuth et al. |
| 3,056,698 A | 10/1962 | Kleesattel et al. |
| 3,089,790 A | 5/1963 | Balamuth et al. |
| 3,113,225 A | 12/1963 | Kleesattel et al. |
| 3,132,548 A | 5/1964 | Livermont |
| 3,133,351 A | 5/1964 | von Seggern |
| 3,202,021 A | 8/1965 | Livermont |
| 3,241,780 A | 3/1966 | Kitselman |
| 3,304,449 A | 2/1967 | Pohlman et al. |
| 3,315,663 A | 4/1967 | Goldfarb |
| 3,401,446 A | 9/1968 | Obeda et al. |
| 3,433,226 A | 3/1969 | Boyd |
| 3,438,824 A | 4/1969 | Balamuth |
| 3,486,361 A | 12/1969 | Vaneman et al. |
| 3,524,085 A | 8/1970 | Shoh |
| 3,526,219 A | 9/1970 | Balamuth |
| 3,528,410 A | 9/1970 | Banko |
| 3,565,062 A | 2/1971 | Kuris .......................... 128/24 |
| 3,589,363 A | 6/1971 | Banko et al. |
| 3,614,484 A | 10/1971 | Shoh |
| 3,660,186 A | 5/1972 | Sager et al. |
| 3,683,736 A | 8/1972 | Loose |
| 3,763,680 A | 10/1973 | Godfrey et al. |
| 3,805,787 A | 4/1974 | Banko |
| 3,809,977 A | 5/1974 | Balamuth et al. |
| 3,840,932 A | 10/1974 | Balamuth et al. |
| 3,853,130 A | 12/1974 | Sheridan |
| 3,861,391 A | 1/1975 | Antonevich et al. |
| 3,890,977 A | 6/1975 | Wilson |
| 3,906,954 A | 9/1975 | Baehr et al. |
| 3,939,033 A | 2/1976 | Grgach et al. |
| 3,955,662 A | 5/1976 | Thackston |
| 3,962,898 A | 6/1976 | Tillmann |
| 3,967,621 A | 7/1976 | Schwarz |
| 3,980,906 A | 9/1976 | Kuris et al. |
| 3,988,782 A | 11/1976 | Dardik et al. |
| 3,990,452 A | 11/1976 | Murry et al. |
| 3,991,929 A | 11/1976 | Smith |
| 4,011,474 A | 3/1977 | O'Neill |
| 4,012,174 A | 3/1977 | Seibel et al. |
| 4,012,647 A | 3/1977 | Balamuth et al. |
| 4,044,174 A | 8/1977 | Carr |
| 4,063,557 A | 12/1977 | Wuchinich et al. |
| 4,069,541 A | 1/1978 | Williams et al. |
| 4,083,996 A | 4/1978 | Tanaka et al. |
| 4,136,700 A | 1/1979 | Broadwin et al. |
| 4,143,130 A | 3/1979 | Imondi et al. |
| 4,144,646 A | 3/1979 | Takemoto et al. ........... 32/40 R |
| 4,157,396 A | 6/1979 | Tanaka et al. |
| 4,164,524 A | 8/1979 | Ward et al. |
| 4,169,984 A | 10/1979 | Parisi |
| 4,174,410 A | 11/1979 | Smith |
| 4,178,935 A | 12/1979 | Gekhman et al. |
| 4,203,429 A | 5/1980 | Vasilevsky et al. |
| 4,203,444 A | 5/1980 | Bonnell et al. |
| 4,223,676 A | 9/1980 | Wuchinich et al. |
| 4,225,803 A | 9/1980 | Goof |
| 4,236,510 A | 12/1980 | Hatter et al. |
| 4,248,232 A | 2/1981 | Engelbrecht et al. |
| 4,265,928 A | 5/1981 | Braun |
| 4,280,233 A | 7/1981 | Raab |
| 4,300,564 A | 11/1981 | Furihata |
| 4,311,147 A | 1/1982 | Hausler |
| 4,315,181 A | 2/1982 | Holze, Jr. |
| 4,316,465 A | 2/1982 | Dotson, Jr. |
| 4,326,903 A | 4/1982 | Summo |
| 4,334,168 A | 6/1982 | Besson et al. |
| 4,335,426 A | 6/1982 | Maxwell et al. |
| 4,352,570 A | 10/1982 | Firth |
| 4,356,590 A | 11/1982 | Goldsmith |
| 4,363,992 A | 12/1982 | Holze, Jr. |
| 4,368,410 A | 1/1983 | Hance et al. |
| 4,385,413 A | 5/1983 | Goldsmith |
| 4,393,734 A | 7/1983 | Thorn et al. |
| 4,395,392 A | 7/1983 | Wolgemuth |
| 4,399,003 A | 8/1983 | Sarig et al. |
| 4,414,045 A | 11/1983 | Wang et al. |
| 4,425,115 A | 1/1984 | Wuchinich |
| 4,428,748 A | 1/1984 | Peyman et al. |
| 4,445,509 A | 5/1984 | Auth |
| 4,447,455 A | 5/1984 | Madaus et al. |
| 4,462,242 A | 7/1984 | Morgenthaler |
| 4,467,678 A | 8/1984 | Lindholm |
| 4,474,180 A | 10/1984 | Angulo |
| 4,479,585 A | 10/1984 | Sandhaus |
| 4,480,642 A | 11/1984 | Stoy et al. |
| 4,483,571 A | 11/1984 | Mishiro |
| 4,486,680 A | 12/1984 | Bonnet et al. |
| 4,493,694 A | 1/1985 | Wuchinich |
| 4,498,025 A | 2/1985 | Takahashi .................... 310/312 |
| 4,504,264 A | 3/1985 | Kelman |
| 4,516,398 A | 5/1985 | Wuchinich |
| 4,523,122 A | 6/1985 | Tone et al. |
| 4,526,571 A | 7/1985 | Wuchinich |
| 4,529,115 A | 7/1985 | Renshaw et al. |
| 4,530,138 A | 7/1985 | Ritter |
| 4,534,819 A | 8/1985 | Payet et al. |
| 4,535,659 A | 8/1985 | Yang |
| 4,535,759 A | 8/1985 | Polk et al. |
| 4,571,520 A | 2/1986 | Saito et al. |
| 4,572,041 A | 2/1986 | Rissmann |
| 4,576,177 A | 3/1986 | Webster, Jr. |
| 4,583,365 A | 4/1986 | John |
| 4,587,958 A | 5/1986 | Noguchi et al. |
| 4,589,415 A | 5/1986 | Haaga |
| 4,601,705 A | 7/1986 | McCoy |
| 4,603,694 A | 8/1986 | Wheeler |
| 4,605,454 A | 8/1986 | Sayovitz et al. |
| 4,607,185 A | 8/1986 | Elbert et al. |
| 4,609,368 A | 9/1986 | Dotson, Jr. |
| 4,620,545 A | 11/1986 | Shene et al. |
| 4,633,119 A | 12/1986 | Thompson |
| 4,634,420 A | 1/1987 | Spinosa et al. |
| 4,642,509 A | 2/1987 | Kumada ...................... 310/323 |
| 4,643,717 A | 2/1987 | Cook et al. |
| 4,647,336 A | 3/1987 | Coenen et al. |
| 4,647,871 A | 3/1987 | Turner, Jr. |
| 4,651,043 A | 3/1987 | Harris et al. |
| 4,652,785 A | 3/1987 | Gabriel et al. |
| 4,652,786 A | 3/1987 | Mishiro ...................... 310/333 |
| 4,655,104 A | 4/1987 | Blattner |
| 4,663,556 A | 5/1987 | Kumada ...................... 310/333 |
| 4,676,975 A | 6/1987 | McGary et al. |
| 4,678,993 A | 7/1987 | Vinnemann et al. ......... 324/208 |
| 4,688,454 A | 8/1987 | Scull |
| 4,690,722 A | 9/1987 | Flood |
| 4,692,139 A | 9/1987 | Stiles |
| 4,696,299 A | 9/1987 | Shene et al. |
| 4,702,236 A | 10/1987 | Tarabichy et al. |
| 4,704,131 A | 11/1987 | Noishiki et al. |
| 4,704,573 A | 11/1987 | Turner, Jr. |
| 4,708,127 A | 11/1987 | Abdelghani |
| 4,713,132 A | 12/1987 | Abel et al. |
| 4,715,078 A | 12/1987 | Howard et al. |
| 4,718,907 A | 1/1988 | Karwoski et al. |
| 4,730,614 A | 3/1988 | Lacruche et al. |
| 4,732,152 A | 3/1988 | Wallsten et al. |

| | | | | | |
|---|---|---|---|---|---|
| 4,732,156 A | 3/1988 | Nakamura | 5,015,227 A | 5/1991 | Broadwin et al. |
| 4,735,625 A | 4/1988 | Davidson | 5,017,379 A | 5/1991 | Lemelson |
| 4,738,666 A | 4/1988 | Fuqua | 5,019,083 A | 5/1991 | Klapper et al. |
| 4,738,667 A | 4/1988 | Galloway | 5,024,234 A | 6/1991 | Leary et al. |
| 4,747,820 A | 5/1988 | Hornlein et al. | 5,026,387 A | 6/1991 | Thomas |
| 4,748,985 A | 6/1988 | Nagasaki | 5,027,792 A | 7/1991 | Meyer |
| 4,748,986 A | 6/1988 | Morrison et al. | 5,040,548 A | 8/1991 | Yock |
| 4,749,437 A | 6/1988 | Welter | 5,045,054 A | 9/1991 | Hood et al. |
| 4,750,488 A | 6/1988 | Wuchinich et al. | 5,046,497 A | 9/1991 | Millar |
| 4,750,902 A | 6/1988 | Wuchinich et al. | 5,049,157 A | 9/1991 | Mittelmeier et al. |
| 4,751,916 A | 6/1988 | Bory | 5,054,492 A | 10/1991 | Scribner et al. |
| 4,756,304 A | 7/1988 | Watanabe | 5,055,101 A | 10/1991 | McCoy |
| 4,756,309 A | 7/1988 | Sachse et al. | 5,057,106 A | 10/1991 | Kasevich et al. |
| 4,758,222 A | 7/1988 | McCoy | 5,057,119 A | 10/1991 | Clark et al. |
| 4,758,293 A | 7/1988 | Samida | 5,057,182 A | 10/1991 | Wuchinich |
| 4,762,668 A | 8/1988 | Loose et al. | 5,058,570 A | 10/1991 | Idemoto et al. |
| 4,770,730 A | 9/1988 | Abe | 5,059,210 A | 10/1991 | Clark et al. |
| 4,771,202 A | 9/1988 | Takahashi .................. 310/312 | 5,061,273 A | 10/1991 | Yock |
| 4,771,782 A | 9/1988 | Millar | 5,062,827 A | 11/1991 | Wiksell |
| 4,791,915 A | 12/1988 | Barsotti et al. | 5,064,765 A | 11/1991 | Karasikov et al. |
| 4,794,912 A | 1/1989 | Lia | 5,069,664 A | 12/1991 | Guess et al. |
| 4,823,723 A | 4/1989 | Brooks | 5,076,276 A | 12/1991 | Sakurai et al. |
| 4,823,783 A | 4/1989 | Willhite, Jr. et al. | 5,102,403 A | 4/1992 | Alt |
| 4,825,851 A | 5/1989 | Cocks et al. | 5,106,741 A | 4/1992 | Marotti et al. |
| 4,828,052 A | 5/1989 | Duran et al. | 5,108,238 A | 4/1992 | Ewing |
| 4,830,002 A | 5/1989 | Semm | 5,109,830 A | 5/1992 | Cho |
| 4,834,102 A | 5/1989 | Schwarzchild et al. | 5,112,300 A | 5/1992 | Ureche |
| 4,838,853 A | 6/1989 | Parisi | 5,116,343 A | 5/1992 | Ams et al. |
| 4,838,859 A | 6/1989 | Strassmann | 5,122,122 A | 6/1992 | Allgood |
| 4,844,081 A | 7/1989 | Northeved et al. | 5,123,903 A | 6/1992 | Quaid et al. |
| 4,846,161 A | 7/1989 | Roger | 5,127,405 A | 7/1992 | Alcala et al. |
| 4,846,174 A | 7/1989 | Willard et al. | 5,129,914 A | 7/1992 | Choi |
| 4,846,790 A | 7/1989 | Hornlein et al. | 5,139,496 A | 8/1992 | Hed |
| 4,850,358 A | 7/1989 | Millar | 5,139,509 A | 8/1992 | Fischer et al. |
| 4,862,573 A | 9/1989 | Kelson et al. | 5,147,316 A | 9/1992 | Castillenti |
| 4,866,491 A | 9/1989 | Solomon et al. | 5,151,085 A | 9/1992 | Sakurai et al. |
| 4,867,141 A | 9/1989 | Nakada et al. | 5,151,099 A | 9/1992 | Young et al. |
| 4,870,953 A | 10/1989 | DonMicheal et al. ...... 128/24 A | 5,152,200 A | 10/1992 | Kaplan |
| 4,872,333 A | 10/1989 | Burnand | 5,152,748 A | 10/1992 | Chastagner |
| 4,873,969 A | 10/1989 | Huebsch | 5,156,143 A | 10/1992 | Bocquet et al. |
| 4,877,037 A | 10/1989 | Ko et al. | 5,163,421 A | 11/1992 | Bernstein et al. |
| 4,880,011 A | 11/1989 | Imade et al. | 5,167,619 A | 12/1992 | Wuchinich .................. 604/22 |
| 4,881,761 A | 11/1989 | Hornlein et al. | 5,169,386 A | 12/1992 | Becker et al. |
| 4,882,777 A | 11/1989 | Narula | 5,171,387 A | 12/1992 | Wuchinich ................. 152/73.3 |
| 4,885,499 A | 12/1989 | Ueha et al. | 5,175,492 A | 12/1992 | Wong et al. |
| 4,886,060 A | 12/1989 | Wiksell | 5,176,141 A | 1/1993 | Bom et al. |
| 4,886,491 A | 12/1989 | Parisi et al. | 5,176,677 A | 1/1993 | Wuchinich .................. 604/356 |
| 4,892,089 A | 1/1990 | Cocks et al. | 5,180,363 A | 1/1993 | Idemoto et al. |
| 4,904,391 A | 2/1990 | Freeman | 5,190,517 A | 3/1993 | Zieve et al. |
| 4,907,572 A | 3/1990 | Borodulin et al. | 5,193,525 A | 3/1993 | Silverstein et al. |
| 4,909,789 A | 3/1990 | Taguchi et al. | 5,195,955 A | 3/1993 | DonMichael |
| 4,917,104 A | 4/1990 | Rebell | 5,201,315 A | 4/1993 | Griffith |
| 4,920,954 A | 5/1990 | Alliger et al. | 5,201,316 A | 4/1993 | Pomeranz et al. |
| 4,922,902 A | 5/1990 | Wuchinich et al. | 5,203,338 A | 4/1993 | Jang |
| 4,924,863 A | 5/1990 | Sterzer | 5,209,719 A | 5/1993 | Baruch et al. |
| 4,931,047 A | 6/1990 | Broadwin et al. | 5,217,465 A | 6/1993 | Steppe |
| 4,931,049 A | 6/1990 | Klimas | 5,221,282 A | 6/1993 | Wuchinich |
| 4,936,281 A | 6/1990 | Stasz | 5,222,937 A | 6/1993 | Kagawa |
| 4,960,410 A | 10/1990 | Pinchuk | 5,222,974 A | 6/1993 | Kensey et al. |
| 4,961,424 A | 10/1990 | Kubota et al. ............. 128/24 A | 5,231,080 A | 7/1993 | Scholkens |
| 4,962,755 A | 10/1990 | King et al. | 5,231,994 A | 8/1993 | Harmjanz |
| 4,963,151 A | 10/1990 | Ducheyne et al. | 5,232,451 A | 8/1993 | Freitas et al. |
| 4,966,131 A | 10/1990 | Houghton et al. | 5,235,964 A | 8/1993 | Abenaim |
| 4,966,148 A | 10/1990 | Millar | 5,240,437 A | 8/1993 | Christian |
| 4,974,581 A | 12/1990 | Wiksell | 5,243,997 A | 9/1993 | Uflacker et al. |
| 4,978,333 A | 12/1990 | Broadwin et al. | 5,248,296 A | 9/1993 | Alliger |
| 4,979,952 A | 12/1990 | Kubota et al. | 5,249,580 A | 10/1993 | Griffith |
| 4,986,808 A | 1/1991 | Broadwin et al. | 5,255,551 A | 10/1993 | Vetter |
| 4,989,583 A | 2/1991 | Hood | 5,255,669 A | 10/1993 | Kubota et al. |
| 4,989,588 A | 2/1991 | Kubota et al. | 5,261,805 A | 11/1993 | Gates |
| 5,003,965 A | 4/1991 | Talish et al. | 5,261,877 A | 11/1993 | Fine et al. |
| 5,003,990 A | 4/1991 | Osypka | 5,263,928 A | 11/1993 | Trauthen et al. |
| 5,015,221 A | 5/1991 | Smith | 5,263,932 A | 11/1993 | Jang |

| Patent No. | Date | Inventor(s) |
|---|---|---|
| 5,267,954 A | 12/1993 | Nita |
| 5,267,958 A | 12/1993 | Buchbinder et al. |
| 5,267,982 A | 12/1993 | Sylvanowicz |
| 5,269,297 A | 12/1993 | Weng et al. |
| 5,271,735 A | 12/1993 | Greenfeld et al. |
| 5,274,297 A | 12/1993 | Hermann et al. ............. 310/361 |
| 5,285,795 A | 2/1994 | Ryan et al. |
| 5,287,775 A | 2/1994 | Moore |
| 5,290,229 A | 3/1994 | Paskar |
| 5,300,021 A | 4/1994 | Wuchinich |
| 5,300,032 A | 4/1994 | Hibbs et al. |
| 5,300,085 A | 4/1994 | Yock |
| 5,304,115 A | 4/1994 | Pflueger et al. |
| 5,304,131 A | 4/1994 | Paskar |
| 5,304,199 A | 4/1994 | Myers |
| 5,306,261 A | 4/1994 | Alliger et al. |
| 5,307,816 A | 5/1994 | Hashimoto et al. |
| 5,311,858 A | 5/1994 | Adair |
| 5,312,328 A | 5/1994 | Nita et al. |
| 5,312,329 A | 5/1994 | Beaty et al. |
| 5,312,427 A | 5/1994 | Shturman |
| 5,315,996 A | 5/1994 | Lundquist |
| 5,318,528 A | 6/1994 | Heaven et al. |
| 5,319,278 A | 6/1994 | Myohga et al. ............. 310/323 |
| 5,323,902 A | 6/1994 | Palmer et al. |
| 5,324,255 A | 6/1994 | Passafaro et al. |
| 5,324,299 A | 6/1994 | Davison et al. |
| 5,325,698 A | 7/1994 | Nagpal et al. |
| 5,326,342 A | 7/1994 | Pflueger et al. |
| 5,329,927 A | 7/1994 | Gardineer et al. |
| 5,330,444 A | 7/1994 | Webler et al. |
| 5,330,482 A | 7/1994 | Gibbs et al. |
| 5,330,497 A | 7/1994 | Freitas et al. |
| 5,331,242 A | 7/1994 | Petri ........................ 310/370 |
| 5,334,160 A | 8/1994 | Ellis |
| 5,334,167 A | 8/1994 | Cocanower |
| 5,334,183 A | 8/1994 | Wuchinich |
| 5,336,184 A | 8/1994 | Teirstein |
| 5,336,234 A | 8/1994 | Vigil et al. |
| 5,336,699 A | 8/1994 | Cooke et al. |
| 5,342,292 A | 8/1994 | Nita et al. |
| 5,344,395 A | 9/1994 | Whalen et al. |
| 5,350,395 A | 9/1994 | Yock |
| 5,351,679 A | 10/1994 | Mayzels et al. |
| 5,353,798 A | 10/1994 | Sieben |
| 5,356,385 A | 10/1994 | Latini |
| 5,356,421 A | 10/1994 | Castro |
| 5,358,505 A | 10/1994 | Wuchinich |
| 5,362,309 A | 11/1994 | Carter |
| 5,366,490 A | 11/1994 | Edwards et al. |
| 5,366,899 A | 11/1994 | Shabalin et al. |
| 5,368,557 A | 11/1994 | Nita et al. |
| 5,368,558 A | 11/1994 | Nita |
| 5,370,602 A | 12/1994 | Kepley |
| 5,380,273 A | 1/1995 | Dubrul et al. |
| 5,380,274 A | 1/1995 | Nita |
| 5,382,228 A | 1/1995 | Nita et al. |
| 5,385,372 A | 1/1995 | Utterberg |
| 5,387,190 A | 2/1995 | Gotanda et al. |
| 5,387,197 A | 2/1995 | Smith et al. |
| 5,388,569 A | 2/1995 | Kepley |
| 5,390,678 A | 2/1995 | Gesswein et al. |
| 5,391,144 A | 2/1995 | Sakurai et al. ................ 604/22 |
| 5,396,902 A | 3/1995 | Brennen et al. |
| 5,397,293 A | 3/1995 | Alliger et al. |
| 5,397,301 A | 3/1995 | Pflueger et al. |
| 5,402,799 A | 4/1995 | Colon et al. |
| 5,403,324 A | 4/1995 | Ciervo et al. |
| 5,405,318 A | 4/1995 | Nita |
| 5,405,341 A | 4/1995 | Martin |
| 5,406,503 A | 4/1995 | Williams, Jr. et al. |
| 5,409,112 A | 4/1995 | Sagstetter |
| 5,417,654 A | 5/1995 | Kelman |
| 5,417,672 A | 5/1995 | Nita et al. |
| 5,419,761 A | 5/1995 | Narayanan et al. |
| 5,421,338 A | 6/1995 | Crowley et al. |
| 5,421,829 A | 6/1995 | Olichney et al. |
| 5,423,797 A | 6/1995 | Adrian et al. |
| 5,423,838 A | 6/1995 | Willard |
| 5,425,704 A | 6/1995 | Sakurai et al. |
| 5,427,118 A | 6/1995 | Nita et al. |
| 5,429,136 A | 7/1995 | Milo et al. |
| 5,431,664 A | 7/1995 | Ureche et al. |
| 5,434,827 A | 7/1995 | Bolorforosh |
| 5,443,443 A | 8/1995 | Shiber |
| 5,443,456 A | 8/1995 | Alliger et al. |
| 5,443,457 A | 8/1995 | Ginn et al. |
| 5,443,468 A | 8/1995 | Johnson |
| 5,445,617 A | 8/1995 | Yoon |
| 5,447,509 A | 9/1995 | Mills et al. |
| 5,449,369 A | 9/1995 | Imran |
| 5,451,233 A | 9/1995 | Yock |
| 5,452,611 A | 9/1995 | Jones et al. |
| 5,454,373 A | 10/1995 | Koger et al. |
| 5,458,584 A | 10/1995 | Ginn et al. |
| 5,458,612 A | 10/1995 | Chin |
| 5,460,595 A | 10/1995 | Hall et al. |
| 5,462,530 A | 10/1995 | Jang |
| 5,464,016 A | 11/1995 | Nicholas et al. |
| 5,464,409 A | 11/1995 | Mohajer |
| 5,464,438 A | 11/1995 | Menaker |
| 5,467,674 A | 11/1995 | Thorn |
| 5,469,853 A | 11/1995 | Law et al. |
| 5,470,322 A | 11/1995 | Horzewski et al. |
| 5,472,441 A | 12/1995 | Edwards et al. |
| 5,474,075 A | 12/1995 | Goldberg et al. |
| 5,474,530 A | 12/1995 | Passafaro et al. |
| 5,474,531 A | 12/1995 | Carter |
| 5,478,353 A | 12/1995 | Yoon |
| 5,478,558 A | 12/1995 | Eibl et al. |
| 5,484,398 A | 1/1996 | Stoddard |
| 5,492,001 A | 2/1996 | Sasaki et al. |
| 5,498,236 A | 3/1996 | Dubrul et al. |
| 5,501,227 A | 3/1996 | Yock |
| 5,505,714 A | 4/1996 | Dassa et al. |
| 5,507,738 A | 4/1996 | Ciervo |
| 5,512,037 A | 4/1996 | Russell et al. |
| 5,516,043 A | 5/1996 | Manna et al. |
| 5,524,620 A | 6/1996 | Rosenschein |
| 5,524,635 A | 6/1996 | Uflacker et al. |
| 5,527,273 A | 6/1996 | Manna et al. |
| 5,527,279 A | 6/1996 | Imran |
| 5,531,664 A | 7/1996 | Adachi et al. |
| 5,536,250 A | 7/1996 | Klein et al. |
| 5,540,656 A | 7/1996 | Pflueger et al. |
| 5,542,917 A | 8/1996 | Nita et al. |
| 5,549,563 A | 8/1996 | Kronner |
| 5,549,576 A | 8/1996 | Patterson et al. |
| 5,562,620 A | 10/1996 | Klein et al. |
| 5,569,276 A | 10/1996 | Jang et al. |
| 5,571,014 A | 11/1996 | Gregory, Jr. et al. |
| 5,571,085 A | 11/1996 | Accisano, III |
| 5,575,772 A | 11/1996 | Lennox |
| 5,580,962 A | 12/1996 | Eibl et al. |
| 5,582,588 A | 12/1996 | Sakurai et al. |
| 5,588,432 A | 12/1996 | Crowley |
| 5,590,653 A | 1/1997 | Aida et al. |
| 5,593,394 A | 1/1997 | Kanesaka et al. |
| 5,599,326 A | 2/1997 | Carter |
| 5,603,445 A | 2/1997 | Hill et al. |
| 5,607,404 A | 3/1997 | Khairkhahan |
| 5,607,440 A | 3/1997 | Danks et al. |
| 5,611,807 A | 3/1997 | O'Boyle |
| 5,622,170 A | 4/1997 | Schulz |
| 5,628,743 A | 5/1997 | Cimino |
| 5,630,427 A | 5/1997 | Hastings |

| | | | | | | |
|---|---|---|---|---|---|---|
| 5,630,797 A | 5/1997 | Diedrich et al. | | 5,904,670 A | 5/1999 | Schreiner |
| 5,630,837 A | 5/1997 | Crowley | | 5,906,628 A | 5/1999 | Miyawaki et al. |
| 5,647,846 A | 7/1997 | Berg et al. | | 5,908,381 A | 6/1999 | Aznoian et al. |
| 5,651,364 A | 7/1997 | Yock | | 5,910,129 A | 6/1999 | Koblish et al. |
| 5,651,776 A | 7/1997 | Appling et al. | | 5,916,192 A | 6/1999 | Nita et al. |
| 5,662,620 A | 9/1997 | Lieber et al. | | 5,916,210 A | 6/1999 | Winston |
| 5,666,970 A | 9/1997 | Smith | | 5,919,163 A | 7/1999 | Glickman |
| 5,669,881 A | 9/1997 | Dunshee | | 5,919,174 A | 7/1999 | Hanson |
| 5,672,172 A | 9/1997 | Zupkas | | 5,920,395 A | 7/1999 | Schulz |
| 5,676,011 A | 10/1997 | Allison | | 5,921,915 A | 7/1999 | Aznoian et al. |
| 5,676,649 A | 10/1997 | Boukhny et al. | | 5,925,016 A | 7/1999 | Chornenky et al. |
| 5,681,296 A | 10/1997 | Ishida | | 5,928,218 A | 7/1999 | Gelbfish |
| 5,685,312 A | 11/1997 | Yock | | 5,931,805 A | 8/1999 | Brisken |
| 5,687,474 A | 11/1997 | Hamzehdoost et al. | | 5,935,096 A | 8/1999 | Barrett |
| 5,688,235 A | 11/1997 | Sakurai et al. | | 5,935,142 A | 8/1999 | Hood |
| 5,690,611 A | 11/1997 | Swartz et al. | | 5,935,143 A | 8/1999 | Hood |
| 5,693,029 A | 12/1997 | Leonhardt | | 5,944,687 A | 8/1999 | Benett et al. |
| 5,704,787 A | 1/1998 | Hickok et al. | | 5,951,480 A | 9/1999 | White et al. |
| 5,707,359 A | 1/1998 | Bufalini | | 5,951,539 A | 9/1999 | Nita et al. |
| 5,709,120 A | 1/1998 | Shilling | | 5,951,583 A | 9/1999 | Jensen et al. |
| 5,713,363 A | 2/1998 | Seward et al. | | 5,957,882 A | 9/1999 | Nita et al. |
| 5,713,848 A | 2/1998 | Dubrul et al. | | 5,961,444 A | 10/1999 | Thompson |
| 5,715,825 A | 2/1998 | Crowley | | 5,964,756 A | 10/1999 | McGaffigan et al. |
| 5,720,300 A | 2/1998 | Fagan et al. | | 5,971,949 A | 10/1999 | Levin et al. |
| 5,720,710 A | 2/1998 | Tachibana et al. | | 5,971,960 A | 10/1999 | Flom et al. |
| 5,722,627 A | 3/1998 | Hoshino | | 5,971,983 A | 10/1999 | Lesh |
| 5,725,494 A | 3/1998 | Brisken | | 5,974,884 A | 11/1999 | Sano et al. |
| 5,728,062 A | 3/1998 | Brisken | | 5,976,093 A | 11/1999 | Jang |
| 5,735,811 A | 4/1998 | Brisken | | 5,980,563 A | 11/1999 | Tu et al. |
| 5,741,225 A | 4/1998 | Lax et al. | | 5,981,444 A | 11/1999 | Sawada et al. |
| 5,749,889 A | 5/1998 | Bacich et al. | | 5,984,882 A | 11/1999 | Rosenschein et al. |
| 5,749,914 A | 5/1998 | Janssen | | 5,984,950 A | 11/1999 | Cragg et al. |
| 5,752,932 A | 5/1998 | Ellis et al. | | 5,987,349 A | 11/1999 | Schulz |
| 5,758,420 A | 6/1998 | Schmidt et al. | | 5,989,208 A | 11/1999 | Nita |
| 5,765,418 A | 6/1998 | Rosenberg | | 5,989,209 A | 11/1999 | Barrett |
| 5,769,868 A | 6/1998 | Yock | | 5,989,274 A | 11/1999 | Davison et al. |
| 5,772,627 A | 6/1998 | Acosta et al. | | 5,993,408 A | 11/1999 | Zaleski |
| 5,775,328 A | 7/1998 | Lowe et al. | | 5,997,497 A | 12/1999 | Nita et al. |
| 5,776,065 A | 7/1998 | Mehmanpazir et al. | | 5,997,523 A | 12/1999 | Jang |
| 5,782,861 A | 7/1998 | Cragg et al. | | 6,001,355 A | 12/1999 | Dowdle |
| 5,797,920 A | 8/1998 | Kim | | 6,004,269 A | 12/1999 | Crowley et al. |
| 5,803,083 A | 9/1998 | Buck et al. | | 6,007,514 A | 12/1999 | Nita |
| 5,810,860 A | 9/1998 | Adrian | | 6,010,476 A | 1/2000 | Saadat |
| 5,813,998 A | 9/1998 | Dias | | 6,010,498 A | 1/2000 | Guglielmi |
| 5,824,042 A | 10/1998 | Lombardi et al. | | 6,017,340 A | 1/2000 | Cassidy et al. |
| 5,827,203 A | 10/1998 | Nita | | 6,017,354 A | 1/2000 | Culp et al. |
| 5,827,229 A | 10/1998 | Auth et al. | | 6,017,359 A | 1/2000 | Gershony et al. |
| 5,830,125 A | 11/1998 | Scribner et al. | | 6,019,777 A | 2/2000 | Mackenzie |
| 5,830,127 A | 11/1998 | DeCastro | | 6,021,694 A | 2/2000 | Beger |
| 5,830,195 A | 11/1998 | Peters et al. | | 6,022,336 A | 2/2000 | Zadno-Azizi et al. |
| 5,833,644 A | 11/1998 | Zadno-Azizi et al. | | 6,022,369 A | 2/2000 | Jacobsen et al. |
| 5,833,650 A | 11/1998 | Imran | | 6,027,515 A | 2/2000 | Cimino |
| 5,836,306 A | 11/1998 | Duane et al. | | 6,032,078 A | 2/2000 | Rudie |
| 5,836,896 A | 11/1998 | Rosenschein | | 6,033,375 A | 3/2000 | Brumbach |
| 5,836,897 A | 11/1998 | Sakurai et al. | | 6,033,411 A | 3/2000 | Preissman |
| 5,840,027 A | 11/1998 | Swartz et al. | | 6,036,671 A | 3/2000 | Frey |
| 5,840,031 A | 11/1998 | Crowley | | 6,036,697 A | 3/2000 | DiCaprio |
| 5,840,151 A | 11/1998 | Munsch | | 6,036,715 A | 3/2000 | Yock |
| 5,843,017 A | 12/1998 | Yoon | | 6,039,693 A | 3/2000 | Seward et al. |
| 5,846,218 A | 12/1998 | Brisken et al. | | 6,039,762 A | 3/2000 | McKay |
| 5,849,009 A | 12/1998 | Bernaz | | 6,045,527 A | 4/2000 | Appelbaum et al. |
| 5,861,023 A | 1/1999 | Vachon | | 6,048,329 A | 4/2000 | Thompson et al. |
| 5,868,773 A | 2/1999 | Danks et al. | | 6,050,949 A | 4/2000 | White et al. |
| 5,868,778 A | 2/1999 | Gershony et al. | | 6,051,772 A | 4/2000 | Cameron et al. |
| 5,875,782 A | 3/1999 | Ferrari et al. | | 6,053,904 A | 4/2000 | Scribner et al. |
| 5,882,347 A | 3/1999 | Mouris-Laan et al. | | RE36,693 E | 5/2000 | Reich |
| 5,890,406 A | 4/1999 | Thorn | | 6,056,722 A | 5/2000 | Jayaraman |
| 5,891,149 A | 4/1999 | Young et al. | | 6,057,798 A | 5/2000 | Burrier et al. |
| 5,895,370 A | 4/1999 | Edwards et al. | | 6,059,789 A | 5/2000 | Dinger et al. |
| 5,895,997 A | 4/1999 | Puskas et al. | | 6,062,001 A | 5/2000 | Kunik |
| 5,897,557 A | 4/1999 | Chin et al. | | 6,062,059 A | 5/2000 | Feldcamp |
| 5,897,569 A | 4/1999 | Kellogg et al. | | 6,068,610 A | 5/2000 | Ellis et al. |
| 5,902,289 A | 5/1999 | Swartz et al. | | 6,077,285 A | 6/2000 | Boukhny ............ 606/169 |

| Patent | Type | Date | Inventor |
|---|---|---|---|
| 6,083,191 | A | 7/2000 | Rose |
| 6,083,501 | A | 7/2000 | Miyata et al. |
| 6,090,118 | A | 7/2000 | McGuckin, Jr. |
| 6,099,464 | A | 8/2000 | Shimizu et al. |
| 6,106,475 | A | 8/2000 | Lowe et al. |
| 6,106,538 | A | 8/2000 | Shiber |
| 6,107,161 | A | 8/2000 | Kitaguro et al. |
| 6,110,142 | A | 8/2000 | Pinchuk et al. |
| 6,110,176 | A | 8/2000 | Shapira |
| 6,113,558 | A | 9/2000 | Rosenschein et al. |
| 6,113,570 | A | 9/2000 | Siegel et al. |
| 6,113,580 | A | 9/2000 | Dolisi |
| 6,123,718 | A | 9/2000 | Tu et al. |
| 6,124,150 | A | 9/2000 | Corisis |
| 6,124,546 | A | 9/2000 | Hayward et al. |
| 6,124,634 | A | 9/2000 | Akram et al. |
| 6,129,672 | A | 10/2000 | Seward et al. |
| 6,146,380 | A | 11/2000 | Racz et al. |
| 6,146,381 | A | 11/2000 | Bowe et al. |
| 6,156,018 | A | 12/2000 | Hassett |
| 6,159,195 | A | 12/2000 | Ha et al. |
| 6,162,053 | A | 12/2000 | Hollander |
| 6,165,197 | A | 12/2000 | Yock |
| 6,190,353 | B1 | 2/2001 | Makower et al. |
| 6,193,683 | B1 | 2/2001 | Ludin et al. |
| 6,200,269 | B1 | 3/2001 | Lin et al. |
| 6,200,315 | B1 | 3/2001 | Gaiser et al. |
| 6,203,516 | B1 | 3/2001 | Kepley |
| 6,203,568 | B1 | 3/2001 | Lombardi et al. |
| 6,224,565 | B1 | 5/2001 | Cimino |
| 6,228,046 | B1 | 5/2001 | Brisken |
| 6,231,514 | B1 | 5/2001 | Lowe et al. |
| 6,231,518 | B1 | 5/2001 | Grabek et al. |
| 6,234,971 | B1 | 5/2001 | Jang |
| 6,235,000 | B1 | 5/2001 | Milo et al. |
| 6,241,703 | B1 | 6/2001 | Levin et al. |
| 6,245,095 | B1 | 6/2001 | Dobak, III et al. |
| 6,247,592 | B1 | 6/2001 | Racicot et al. |
| 6,258,798 | B1 | 7/2001 | Wallentin |
| 6,262,062 | B1 | 7/2001 | Clemens |
| 6,270,460 | B1 | 8/2001 | McCartan et al. |
| 6,277,084 | B1 | 8/2001 | Abele et al. |
| 6,279,743 | B1 | 8/2001 | Ballard et al. |
| 6,280,413 | B1 | 8/2001 | Clark et al. |
| 6,283,951 | B1 | 9/2001 | Flaherty et al. |
| 6,287,271 | B1 | 9/2001 | Dubrul et al. |
| 6,287,272 | B1 | 9/2001 | Brisken et al. |
| 6,290,662 | B1 | 9/2001 | Morris et al. |
| 6,290,673 | B1 | 9/2001 | Shanley |
| 6,293,725 | B1 | 9/2001 | Winkvist |
| 6,296,658 | B1 | 10/2001 | Gershony et al. |
| 6,303,635 | B1 | 10/2001 | Kawai et al. |
| 6,306,097 | B1 | 10/2001 | Park et al. |
| 6,307,156 | B1 | 10/2001 | Avellanet |
| 6,309,379 | B1 | 10/2001 | Willard et al. |
| 6,312,406 | B1 | 11/2001 | Jayaraman |
| 6,322,541 | B2 | 11/2001 | West et al. |
| 6,329,778 | B1 | 12/2001 | Culp et al. |
| 6,346,091 | B1 | 2/2002 | Jacobsen et al. |
| 6,348,039 | B1 | 2/2002 | Flachman et al. |
| 6,358,252 | B1 | 3/2002 | Shapira |
| 6,364,840 | B1 | 4/2002 | Crowley |
| 6,364,841 | B1 | 4/2002 | White et al. |
| 6,368,611 | B1 | 4/2002 | Whitbourne et al. |
| 6,376,513 | B1 | 4/2002 | Akahane et al. |
| 6,383,151 | B1 | 5/2002 | Diederich et al. |
| 6,391,042 | B1 | 5/2002 | Cimino |
| 6,396,293 | B1 | 5/2002 | Vinther et al. |
| 6,398,776 | B1 | 6/2002 | Sekino et al. |
| 6,398,792 | B1 | 6/2002 | O'Connor |
| 6,410,560 | B1 | 6/2002 | Akahane et al. |
| 6,416,511 | B1 | 7/2002 | Lesh et al. |
| 6,416,530 | B2 | 7/2002 | DeVries et al. |
| 6,416,737 | B1 | 7/2002 | Manolagas et al. |
| 6,419,644 | B1 | 7/2002 | White et al. |
| 6,433,464 | B2 | 8/2002 | Jones |
| 6,440,726 | B1 | 8/2002 | Resnick |
| 6,440,947 | B1 | 8/2002 | Barron et al. |
| 6,443,903 | B1 | 9/2002 | White et al. |
| 6,450,975 | B1 | 9/2002 | Brennan et al. |
| 6,451,303 | B1 | 9/2002 | Whitehouse et al. |
| 6,454,737 | B1 | 9/2002 | Nita et al. |
| 6,454,757 | B1 | 9/2002 | Nita et al. |
| 6,457,365 | B1 | 10/2002 | Stephens et al. |
| 6,458,375 | B1 | 10/2002 | Gertzman et al. |
| 6,462,172 | B1 | 10/2002 | Maclennan et al. |
| 6,464,660 | B2 | 10/2002 | Brisken et al. |
| 6,469,419 | B2 | 10/2002 | Kato et al. ............. 310/323.02 |
| 6,471,656 | B1 | 10/2002 | Shalman et al. |
| 6,475,185 | B1 | 11/2002 | Rauker et al. |
| 6,478,751 | B1 | 11/2002 | Krueger et al. |
| 6,482,218 | B1 | 11/2002 | Tran |
| 6,485,481 | B1 | 11/2002 | Pfeiffer |
| 6,491,710 | B2 | 12/2002 | Satake |
| 6,491,711 | B1 | 12/2002 | Durcan |
| 6,494,883 | B1 | 12/2002 | Ferree |
| 6,494,885 | B1 | 12/2002 | Dhindsa |
| 6,494,891 | B1 | 12/2002 | Cornish et al. |
| 6,494,893 | B2 | 12/2002 | Dubrul et al. |
| 6,497,667 | B1 | 12/2002 | Miller et al. |
| 6,497,698 | B1 | 12/2002 | Fonger et al. |
| 6,503,223 | B1 | 1/2003 | Sekido et al. |
| 6,508,781 | B1 | 1/2003 | Brennan et al. |
| 6,508,782 | B1 | 1/2003 | Evans et al. |
| 6,509,348 | B1 | 1/2003 | Ogletree |
| 6,511,492 | B1 | 1/2003 | Rosenbluth et al. |
| 6,512,957 | B1 | 1/2003 | Witte |
| 6,514,210 | B2 | 2/2003 | Ohara et al. |
| 6,522,929 | B2 | 2/2003 | Swing |
| 6,524,251 | B2 | 2/2003 | Rabiner et al. ............. 600/439 |
| 6,527,115 | B2 | 3/2003 | Rabiner et al. |
| 6,530,923 | B1 | 3/2003 | Dubrul et al. |
| 6,544,276 | B1 | 4/2003 | Azizi |
| 6,544,279 | B1 | 4/2003 | Hopkins et al. |
| 6,544,541 | B1 | 4/2003 | Zahradka |
| 6,547,724 | B1 | 4/2003 | Soble et al. |
| 6,551,269 | B2 | 4/2003 | Clemens et al. |
| 6,551,327 | B1 | 4/2003 | Dhindsa |
| 6,551,337 | B1 | 4/2003 | Rabiner et al. ............. 606/169 |
| 6,558,334 | B2 | 5/2003 | Shalman et al. |
| 6,569,109 | B2 | 5/2003 | Sakurai et al. |
| 6,569,148 | B2 | 5/2003 | Bagaoisan et al. |
| 6,572,555 | B2 | 6/2003 | White et al. |
| 6,575,959 | B1 | 6/2003 | Sarge et al. |
| 6,575,993 | B1 | 6/2003 | Yock |
| 6,577,042 | B2 | 6/2003 | Lee et al. |
| 6,579,277 | B1 | 6/2003 | Rabiner et al. ............. 604/525 |
| 6,579,279 | B1 | 6/2003 | Rabiner et al. ............. 604/528 |
| 6,579,302 | B2 | 6/2003 | Duerig et al. |
| 6,585,657 | B2 | 7/2003 | Yock |
| 6,589,253 | B1 | 7/2003 | Cornish et al. |
| 6,592,548 | B2 | 7/2003 | Jayaraman |
| 6,596,020 | B2 | 7/2003 | Vardi et al. |
| 6,605,074 | B2 | 8/2003 | Zadno-Azizi et al. |
| 6,611,793 | B1 | 8/2003 | Burnside et al. |
| 6,615,080 | B1 | 9/2003 | Unsworth et al. |
| 6,617,760 | B1 | 9/2003 | Peterson et al. |
| 6,620,113 | B1 | 9/2003 | White et al. |
| 6,626,853 | B2 | 9/2003 | White et al. |
| 6,626,926 | B2 | 9/2003 | Friedman et al. |
| 6,629,948 | B2 | 10/2003 | Rockley et al. |
| 6,645,149 | B1 | 11/2003 | Smith |
| 6,645,152 | B1 | 11/2003 | Jung et al. |
| 6,647,755 | B2 | 11/2003 | Rabiner et al. |
| 6,648,881 | B2 | 11/2003 | KenKnight et al. |
| 6,652,547 | B2 | 11/2003 | Rabiner et al. ............. 606/159 |

| | | | |
|---|---|---|---|
| 6,655,386 B1 | 12/2003 | Makower et al. | |
| 6,660,013 B2 | 12/2003 | Rabiner et al. | 606/128 |
| 6,669,665 B2 | 12/2003 | Jayaraman | |
| 6,679,873 B2 | 1/2004 | Rabiner et al. | 604/528 |
| 6,682,556 B1 | 1/2004 | Ischinger | |
| 6,689,086 B1 | 2/2004 | Nita et al. | |
| 6,689,087 B2 | 2/2004 | Pal et al. | |
| 6,692,460 B1 | 2/2004 | Jayaraman | |
| 6,695,781 B2 | 2/2004 | Rabiner et al. | 600/439 |
| 6,695,782 B2 | 2/2004 | Ranucci et al. | 600/439 |
| 6,702,748 B1 | 3/2004 | Nita et al. | |
| 6,702,750 B2 | 3/2004 | Yock | |
| 6,712,766 B2 | 3/2004 | Harada | |
| 6,723,451 B1 * | 4/2004 | McCullough et al. | 428/611 |
| 6,726,698 B2 | 4/2004 | Cimino | |
| D489,973 S | 5/2004 | Root et al. | |
| 6,730,037 B2 | 5/2004 | Jang | |
| 6,730,048 B1 | 5/2004 | Hare et al. | 601/2 |
| 6,733,451 B2 | 5/2004 | Rabiner et al. | 600/439 |
| 6,760,165 B2 | 7/2004 | Wulff et al. | |
| 6,761,690 B2 | 7/2004 | Sakurai et al. | |
| 6,790,204 B2 | 9/2004 | Zadno-Azizi et al. | |
| 6,802,835 B2 | 10/2004 | Rabiner et al. | |
| 6,840,952 B2 | 1/2005 | Saker et al. | |
| 6,849,062 B2 | 2/2005 | Kantor | |
| 6,855,123 B2 | 2/2005 | Nita | |
| 6,855,125 B2 | 2/2005 | Shanley | |
| 6,860,876 B2 | 3/2005 | Chen | |
| 6,866,670 B2 | 3/2005 | Rabiner et al. | |
| 6,878,106 B1 | 4/2005 | Herrmann | |
| 6,887,257 B2 | 5/2005 | Salahieh et al. | |
| 6,908,472 B2 | 6/2005 | Wiener et al. | |
| 6,921,411 B2 | 7/2005 | Yock | |
| 6,923,788 B2 | 8/2005 | Kantor | |
| 6,929,632 B2 | 8/2005 | Nita et al. | |
| 6,939,317 B2 | 9/2005 | Zacharias | |
| 6,942,620 B2 | 9/2005 | Nita et al. | |
| 6,942,677 B2 | 9/2005 | Nita et al. | |
| 6,966,891 B2 | 11/2005 | Ookubo et al. | |
| 6,984,220 B2 | 1/2006 | Wuchinich | |
| 2001/0047166 A1 | 11/2001 | Wuchinich | 606/1 |
| 2002/0007130 A1 | 1/2002 | Burbank et al. | |
| 2002/0016565 A1 | 2/2002 | Zadno-Azizi et al. | |
| 2002/0029014 A1 | 3/2002 | Jayaraman | |
| 2002/0029054 A1 | 3/2002 | Rabiner et al. | |
| 2002/0055754 A1 | 5/2002 | Ranucci et al. | |
| 2002/0077550 A1 | 6/2002 | Rabiner et al. | |
| 2002/0077643 A1 | 6/2002 | Rabiner et al. | |
| 2002/0082503 A1 | 6/2002 | Chandrasekaran et al. | |
| 2002/0091407 A1 | 7/2002 | Zadno-Azizi et al. | |
| 2002/0095141 A1 | 7/2002 | Belef et al. | |
| 2002/0107446 A1 | 8/2002 | Rabiner et al. | |
| 2003/0009125 A1 | 1/2003 | Nita et al. | |
| 2003/0045835 A1 | 3/2003 | Anderson et al. | |
| 2003/0045887 A1 | 3/2003 | Sakurai et al. | |
| 2003/0048037 A1 | 3/2003 | Boyd | |
| 2003/0074006 A1 | 4/2003 | Mowry et al. | |
| 2003/0114732 A1 | 6/2003 | Webler et al. | |
| 2003/0120208 A1 | 6/2003 | Houser et al. | |
| 2003/0125751 A1 | 7/2003 | Griffin et al. | |
| 2003/0176791 A1 | 9/2003 | Rabiner et al. | |
| 2003/0181923 A1 | 9/2003 | Vardi | |
| 2003/0197958 A1 | 10/2003 | Wulff et al. | |
| 2003/0212331 A1 | 11/2003 | Fenton et al. | |
| 2003/0225332 A1 | 12/2003 | Okada et al. | |
| 2003/0236539 A1 | 12/2003 | Rabiner et al. | |
| 2004/0019266 A1 | 1/2004 | Marciante et al. | |
| 2004/0024393 A1 | 2/2004 | Nita et al. | |
| 2004/0024402 A1 | 2/2004 | Nita | |
| 2004/0039311 A1 | 2/2004 | Nita et al. | |
| 2004/0039375 A1 | 2/2004 | Miyazawa | |
| 2004/0059227 A1 | 3/2004 | Nita et al. | |
| 2004/0059280 A1 | 3/2004 | Makower et al. | |
| 2004/0068189 A1 | 4/2004 | Wilson et al. | |
| 2004/0097996 A1 | 5/2004 | Rabiner et al. | |
| 2004/0106866 A1 | 6/2004 | Ookubo et al. | |
| 2004/0119287 A1 | 6/2004 | Williams et al. | |
| 2004/0138570 A1 | 7/2004 | Nita et al. | |
| 2004/0167507 A1 | 8/2004 | Nita et al. | |
| 2004/0199228 A1 | 10/2004 | Wilson | |
| 2004/0204670 A1 | 10/2004 | Nita et al. | |
| 2004/0204729 A1 | 10/2004 | Cimino | |
| 2004/0210140 A1 | 10/2004 | Rabiner et al. | |
| 2004/0213866 A1 | 10/2004 | Wulff et al. | |
| 2004/0243052 A1 | 12/2004 | Kauphusman et al. | |
| 2005/0043629 A1 | 2/2005 | Rabiner et al. | |
| 2005/0059991 A1 | 3/2005 | Shanley | |
| 2005/0070794 A1 | 3/2005 | Deal et al. | |
| 2005/0101870 A1 | 5/2005 | Yamaguchi et al. | |
| 2005/0101906 A1 | 5/2005 | Nita | |
| 2005/0113688 A1 | 5/2005 | Nita et al. | |
| 2005/0119606 A1 | 6/2005 | Nita | |
| 2005/0124877 A1 | 6/2005 | Nita et al. | |
| 2005/0171570 A1 | 8/2005 | Yock | |
| 2005/0209677 A1 | 9/2005 | Shaked | |
| 2005/0240165 A1 | 10/2005 | Miki et al. | |
| 2005/0245951 A1 | 11/2005 | Nita et al. | |
| 2005/0277577 A1 | 12/2005 | Hunter et al. | |
| 2005/0283080 A1 | 12/2005 | Nita et al. | |

FOREIGN PATENT DOCUMENTS

| | | |
|---|---|---|
| CA | 2320300 | 8/1999 |
| CA | 2 362 689 | 9/2000 |
| DE | 428980 | 5/1926 |
| DE | 203 229 | 10/1983 |
| DE | 37 31 482 | 4/1988 |
| EP | 0 121 491 | 10/1984 |
| EP | 0 243 298 | 10/1987 |
| EP | 0 293 472 | 12/1988 |
| EP | 0 316 796 | 5/1989 |
| EP | 0 353 294 | 2/1990 |
| EP | 0 493 047 | 7/1992 |
| EP | 0 541 249 | 5/1993 |
| EP | 0 542 103 | 5/1993 |
| EP | 0 891 744 | 1/1999 |
| FR | 461395 | 12/1913 |
| FR | 2 614 524 | 11/1988 |
| GB | 19559 | 9/1899 |
| GB | 1 371 335 | 10/1974 |
| GB | 2 032 221 | 4/1980 |
| GB | 2 325 192 | 11/1998 |
| WO | WO 87/01276 | 3/1987 |
| WO | WO 89/06515 | 7/1989 |
| WO | WO 90/01300 | 2/1990 |
| WO | WO 90/10423 | 9/1990 |
| WO | WO 91/07138 | 5/1991 |
| WO | WO 92/04071 | 3/1992 |
| WO | WO 92/11815 | 7/1992 |
| WO | WO 93/16646 | 9/1993 |
| WO | WO 95/03740 | 2/1995 |
| WO | WO 96/07377 | 3/1996 |
| WO | WO 98/35721 | 8/1998 |
| WO | WO 98/55032 | 12/1998 |
| WO | WO 99/16360 | 4/1999 |
| WO | WO 99/33404 | 7/1999 |
| WO | WO 99/35982 | 7/1999 |
| WO | WO 99/39647 | 8/1999 |
| WO | WO 00/21444 | 4/2000 |
| WO | WO 00/53263 | 9/2000 |

OTHER PUBLICATIONS

BBI Newsletter, vol. XIII, No. 3, p. 44, Biomedical Business International, 1524 Brookhollow Drive, Santa Ana, California 92705 (1990).

Beckenbaugh, R.D. and M.S. Ilstrup, *Total Hip Arthroplasty*, J. Bone and Joint Surgery, vol. 60A, pp. 308-314 (1978).

Brochure, Endo-Urology—A Breakthrough in Ultrasonic Lithotripsy, Karl Storz Endoscopy—America, Inc. (1984).

Brochure, Instruments and Apparatus for Lithotripsy, Richard Wolf GmbH, Knittlinger, West Germany (1984).

Brochure, Percutaneous Low Pressure Universal Nephroscope, Richard Wolf, Knittlinger, West Germany (1984).

Cameron, Proximal Femoral Osteotomy in Difficult Revision Hip Surgery: How to Revise the Unrevisable, 18 Contemp. Orthopaedics 565 (1989).

Caspar, Current Development of Instrumentation for Arthroscopy, *Clinics in Sports Medicine*, 6:3 (1987), pp. 626-627.

Chaussy et al., "Transurethral Ultrasonic Ureterolithotripsy Using a Solid-Wire Probe," *Urology*, 29(5):531-532 (May 1987).

De Puy Inc., Catalog (1966).

Eisner, Physical Acoustics, 1964, pp. 353-363.

Emsinger, Ultrasonics, 1988, pp. 419-492.

Ensminger, *Ultrasonics: Fundamentals, Technology, Applications*, pp. 462-467, Marcel Dekker Inc. (1988).

Epstein et al., Surgical Management of Extensive Intramedullary Spinal Cord Astrocytoma in Children, Concepts in Pediatric Neurosurgery, 2, (1982) pp. 29-44.

Goliamina, "*Ultrasonic Surgery*", Proceedings of the Eighth Int'l. Cong. On Acoustics, London, 1974, pp. 63-69.

Gray, "Endovascular treatment of peripheral arterial disease," *Journal of the American Osteopathic Association*, 100(10):S15-S20 (Supplement to Oct. 2000).

Harris et al., A New Technique for Removal of Broken Femoral Stems in Total Hip Replacement, 63-A J. Bone & Joint Surgery 843 (1981).

Johnson, Arthroscopic Surgery: Principles and Practice (3rd Edition), Verlag Springer (1986), pp. 244-245.

Karpman et al., The Lithotriptor and Its Potential Use in the Revision of Total Hip Arthroplasty, 16 Orthopaedic Rev. 81 (1987).

Klapper and Caillouette, "*The Use of Ultrasonic Tools in Revision Arthoplasty Procedures*", 20:3 Contemporary Orthopaedics, pp. 273-279 (Mar. 1990).

Krawitt et al., Ultrasonic Aspiration of Prostate, Bladder Tumors and Stones, *Urology*, 30:6 (1987).

Lin, Posterior Lumbar Interbody Fusion Technique: Complications and Pitfalls, 193 Clinical Orthopaedics and Related Research 90 (1985).

Malloy et al., Endoscopis Ultrasonic Aspiration of the Prostate, Bladder Tumors and Stones, Journal of Urology Supplement, May 1989.

Malloy et al., Transurethral Ultrasonic Aspiration of the Prostrate, A.U.A., May 1989.

McClelland et al., Atraumatic Removal of a Well-Fixed Porous Ingrowth Hip Prosthesis, 15 Orthopaedic Rev. 75 (1986).

Moreland et al., *Techniques for Removal of Prosthesis and Cement in Total Hip Revisional Surgery*, Contemporary Orthopaedics, V. 21, No. 6, pp. 595-635, 1990.

Moreland et al., The Window Technique for the Removal of Broken Femoral Stems in Total Hip Replacement, 212 Clinical Orthopaedics and Related Research 245 (1986).

Neppiras, The Pre-Stressed Piezoelectric Sandwich Transducer, 1973, pp. 295-302.

Rayleigh, The Theory of Sound, vol. 1, 1894, pp. 255-305.

Richards Mfg. Co., Orthopedic Catalog (1981).

Richmond et al., Evaluation of the Histopathology of Brain Tumor Tisue Obtained by Ultrasonic Aspiration, *Neurosurgery*, 13:4 (1983), pp. 415-419.

Rozenberg, Sources of High-Intensity Ultrasound, vol. 2, 1973, pp. 111-114.

Sahagian, Richard, "Critical Insight: Marking Devices with Radiopaque Coatings," May 1999, *Medical Device & Diagnostic Industry Magazine* (http://www.devicelink.com/mddi/archive/99/05/011.html).

Schwartz, Jr. et al., Femoral Fracture During Non-Cemented Total Hip Arthroplasty, 71-A J. Bone & Joint Surgery 1135 (1989).

Sternlieb et al., Ultrasonic Restoration of Severely Calcified Aortic Valve, *The Lancet*, Aug. 20, 1988, p. 446.

Weis, Jr., A Sonic Tool for Spinal Fusion, 8 Orthopedic Clinics of North Am. 43 (1977).

Wick et al., "Tool and Manufacturing Engineers Handbood," Fourth Edition, vol. II, Forming, Society of Manufacturing Engineers, Dearbord, Michigan, 1983-1984, pp. 13-1 through 13-2 (*spelling error?*).

Zhou et al., Effect of Press-Fit Femoral Stems on Strains in the Femur, 5 J. Arthroplasty 71 (1990).

\* cited by examiner

APPARATUS AND METHOD FOR AN ULTRASONIC MEDICAL DEVICE OPERATING IN TORSIONAL AND TRANSVERSE MODES

RELATED APPLICATIONS

None.

FIELD OF THE INVENTION

The present invention relates to ultrasonic medical devices, and more particularly to an apparatus and method of using an ultrasonic probe operating in torsional and transverse modes.

BACKGROUND OF THE INVENTION

The presence of biological material in various parts of the human body can lead to complications ranging from artery disease, heart attack, stroke and in some cases death. The safe and effective destruction of the biological material that causes these complications is an important endeavor in the medical field. A variety of prior art instruments and methods destroy biological material in the human body.

Prior art medical instruments used to destroy biological material in the body suffer from several limitations. Prior art medical instruments are large, making it difficult for medical professionals to utilize them. Prior art medical instruments utilize high power levels that can adversely affect areas surrounding the treatment area and the patient. Procedures using prior art medical instruments are time consuming in comparison with other methods such as surgical excision.

Prior art medical instruments have relied on longitudinal vibrations of the tip of the instrument. By creating longitudinal vibrations of the tip, the tip of the prior art medical instrument must contact the biological material and, similar to a jackhammer, remove the biological material through successive motion of the tip of the instrument. In many cases, the prior art instruments operating in a longitudinal mode have a tip having both a small cross sectional area and a small surface area, thereby removing small amounts of biological material and increasing the overall time of the medical procedure.

For example, U.S. Pat. No. 4,961,424 to Kubota et al. discloses an ultrasonic treatment device operating in a longitudinal mode that is urged or brought into contact with an area to be treated, with energy delivered to the tip of the device. U.S. Pat. No. 4,870,953 to DonMicheal et al. discloses an intravascular ultrasonic catheter/probe and method for treating intravascular blockage that delivers ultrasonic energy via a bulbous tip of the instrument where the bulbous tip is placed in contact with a blockage. U.S. Pat. No. 5,391,144 to Sakurai et al. discloses an ultrasonic treatment apparatus that includes an instrument operating in a longitudinal mode that emulsifies tissue at the tip of the instrument. Therefore, there remains a need in the art for a device that can safely and effectively destroy a large area of biological material in a time efficient manner.

Torsional mode vibration of objects is known in the art. However, the prior art does not describe the torsional mode vibration of a medical device. Further, the prior art requires additional objects to be attached to the prior art instruments, thereby preventing a minimally invasive solution of destroying biological material using torsional mode vibration. For example, U.S. Pat. No. 4,771,202 and U.S. Pat. No. 4,498,025 both to Takahashi disclose a tuning fork using the fundamental vibration of a flexural mode coupled with the fundamental mode of torsion. The fundamental frequency of the torsional mode is adjusted by placing masses near the side edges of the tine tips. U.S. Pat. No. 4,652,786 to Mishiro discloses a torsional vibration apparatus having a plurality of electrodes formed on the two surfaces of a circular member of electrostrictive material. Therefore, there remains a need in the art for an apparatus and a method of destroying biological material that utilizes a medical device that can vibrate in a torsional mode to destroy the biological material in the body in a time efficient manner.

The prior art does not provide a solution for destroying biological material in a safe, effective and time efficient manner. The prior art does not provide an effective solution for increasing a surface area for biological material destruction. Prior art ultrasonic instruments are limited in that they require contact between the device and the biological material and only treat the biological material using the tip of the ultrasonic instrument. Therefore, there remains a need in the art for an apparatus and a method for an ultrasonic medical device operating in a torsional mode and a transverse mode to ablate biological material in a safe, effective and time efficient manner.

SUMMARY OF THE INVENTION

The present invention provides an apparatus and a method for an ultrasonic medical device operating in a torsional mode and a transverse mode to treat a biological material. The present invention is an ultrasonic medical device comprising an ultrasonic probe having a proximal end, a distal end and a longitudinal axis therebetween. The ultrasonic medical device includes a transducer for creating a torsional vibration of the ultrasonic probe. A coupling engages the proximal end of the ultrasonic probe to a distal end of the transducer. An ultrasonic energy source engaged to a proximal end of the transducer produces an electrical energy to power the ultrasonic medical device. The torsional vibration of the ultrasonic probe induces a transverse vibration along an active area of the ultrasonic probe, the active area supporting the torsional vibration and the transverse vibration.

The present invention is a medical device comprising an elongated, flexible probe comprising a proximal end, a distal end and a longitudinal axis between the proximal end and the distal end. The medical device includes a transducer that converts electrical energy into mechanical energy, creating a torsional vibration along the longitudinal axis of the elongated, flexible probe. A coupling engages the proximal end of the elongated, flexible probe to a distal end of the transducer. An ultrasonic energy source engaged to a proximal end of the transducer provides electrical energy to the transducer. The torsional vibration induces a transverse vibration along the longitudinal axis of the elongated, flexible probe.

The present invention is a method of treating a biological material in a body with an ultrasonic medical device comprising: providing an ultrasonic probe having a proximal end, a distal end and a longitudinal axis therebetween; moving the ultrasonic probe to a treatment site of the biological material to place the ultrasonic probe in communication with the biological material; activating an ultrasonic energy source engaged to the ultrasonic probe to produce an ultrasonic energy that is converted into a torsional vibration of the ultrasonic probe; and inducing a transverse vibration in an active area of the ultrasonic probe by the torsional vibration wherein the active area of the ultrasonic probe supports the torsional vibration and the transverse vibration.

The present invention is a method of removing a biological material in a body comprising providing an ultrasonic medical device comprising a flexible probe having a proximal end, a distal end and a longitudinal axis between the proximal end and the distal end. The flexible probe is moved in the body and placed in communication with the biological material. An ultrasonic energy source of the ultrasonic medical device is activated to produce an electrical signal that drives a transducer of the ultrasonic medical device to produce a torsional vibration of the flexible probe. The torsional vibration induces a transverse vibration along the longitudinal axis of the ultrasonic probe.

The present invention provides an apparatus and a method for an ultrasonic medical device operating in a torsional mode and a transverse mode. The active area of the ultrasonic probe operating in the torsional mode and the transverse mode is vibrated in a direction not parallel to the longitudinal axis of the ultrasonic probe while equally spaced points along the active area are vibrated back and forth in a short arc in a plane parallel to the longitudinal axis along the active area of the ultrasonic probe. The present invention provides an ultrasonic medical device that is simple, user-friendly, time efficient, reliable and cost effective.

BRIEF DESCRIPTION OF THE DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention.

Figure 1:
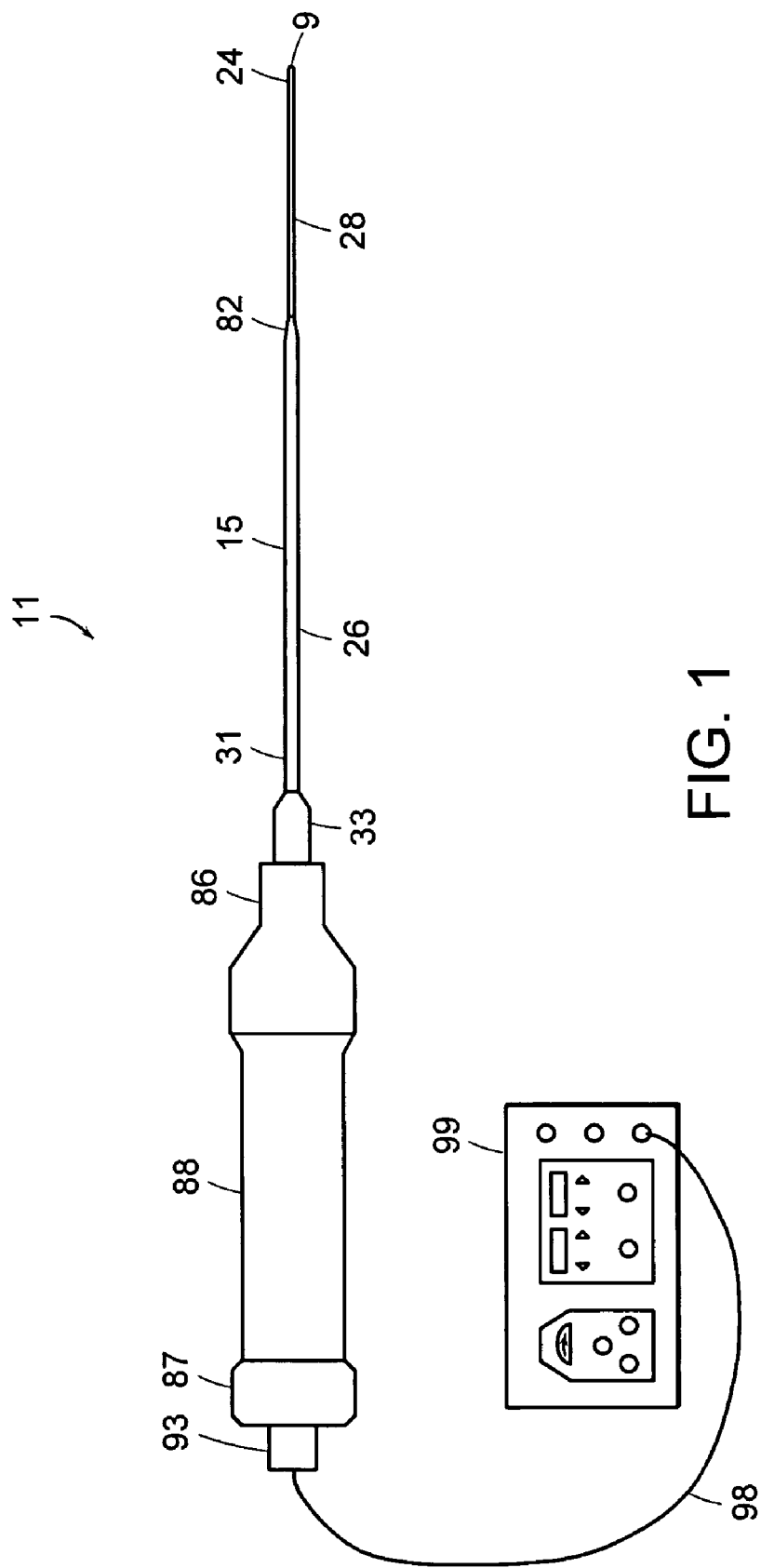
FIG. 1 is a side plan view of an ultrasonic medical device of the present invention capable of operating in a torsional mode and a transverse mode.

While the above-identified drawings set forth preferred embodiments of the present invention, other embodiments of the present invention are also contemplated, as noted in the discussion. This disclosure presents illustrative embodiments of the present invention by way of representation and not limitation. Numerous other modifications and embodiments can be devised by those skilled in the art which fall within the scope and spirit of the principles of the present invention.

DETAILED DESCRIPTION

The present invention provides an apparatus and a method for using an ultrasonic medical device vibrating in a torsional mode and transverse mode to treat a biological material. The ultrasonic medical device comprises an ultrasonic probe, a transducer, a coupling engaging a proximal end of the ultrasonic probe to a distal end of the transducer and an ultrasonic energy source engaged to a proximal end of the transducer. The ultrasonic energy source produces an ultrasonic energy that is transmitted to the transducer, where the transducer creates a torsional vibration of the ultrasonic probe. The torsional vibration induces a transverse vibration along an active area of the ultrasonic probe, creating a plurality of nodes and a plurality of anti-nodes along the active area resulting in cavitation along the active area. The active area of the ultrasonic probe supports the torsional vibration and the transverse vibration.

The following terms and definitions are used herein:

"Ablate" as used herein refers to removing, clearing, destroying or taking away a biological material. "Ablation" as used herein refers to a removal, clearance, destruction, or taking away of the biological material.

"Node" as used herein refers to a region of a minimum energy emitted by an ultrasonic probe at or proximal to a specific location along a longitudinal axis of the ultrasonic probe.

"Anti-node" as used herein refers to a region of a maximum energy emitted by an ultrasonic probe at or proximal to a specific location along a longitudinal axis of the ultrasonic probe.

"Probe" as used herein refers to a device capable of propagating an energy emitted by the ultrasonic energy source along a longitudinal axis of the ultrasonic probe, resolving the energy into an effective cavitational energy at a specific resonance (defined by a plurality of nodes and a plurality of anti-nodes along an "active area" of the probe) and is capable of an acoustic impedance transformation of an ultrasound energy to a mechanical energy.

"Biological material" as used herein refers to a collection of a matter including, but not limited to, a group of similar cells, intravascular blood clots or thrombus, fibrin, calcified plaque, calcium deposits, occlusional deposits, atherosclerotic plaque, fatty deposits, adipose tissues, atherosclerotic cholesterol buildup, fibrous material buildup, arterial stenoses, minerals, high water content tissues, platelets, cellular debris, wastes and other occlusive materials.

"Vibration" as used herein refers to movement wherein portions of an object move alternately in opposite directions from a position of equilibrium. Vibration also refers to motion, oscillation and wave propagation.

An ultrasonic medical device capable of operating in a torsional mode and transverse mode is illustrated generally at 11 in FIG. 1. The ultrasonic medical device 11 includes an ultrasonic probe 15 which is coupled to an ultrasonic energy source or generator 99 for the production of an ultrasonic energy. A handle 88, comprising a proximal end 87 and a distal end 86, surrounds a transducer within the handle 88. The transducer, having a proximal end engaging the ultrasonic energy source 99 and a distal end coupled to a proximal end 31 of the ultrasonic probe 15, transmits the ultrasonic energy to the ultrasonic probe 15. A connector 93 and a connecting wire 98 engage the ultrasonic energy source 99 to the transducer. The ultrasonic probe 15 includes the proximal end 31, a distal end 24 that ends in a probe tip 9 and a longitudinal axis between the proximal end 31 and the distal end 24. In a preferred embodiment of the present invention shown in FIG. 1, a diameter of the ultrasonic probe decreases from a first defined interval 26 to a second defined interval 28 along the longitudinal axis of the ultrasonic probe 15 over a diameter transition 82. A coupling 33 that engages the proximal end 31 of the ultrasonic probe 15 to the transducer within the handle 88 is illustrated generally in FIG. 1. In a preferred embodiment of the present invention, the coupling is a quick attachment-detachment system. An ultrasonic medical device with a quick attachment-detachment system is described in the Assignee's co-pending patent applications U.S. Ser. No. 09/975,725; U.S. Ser. No. 10/268,487 and U.S. Ser. No. 10/268,843, and the entirety of all these applications are hereby incorporated herein by reference.

Figure 2:
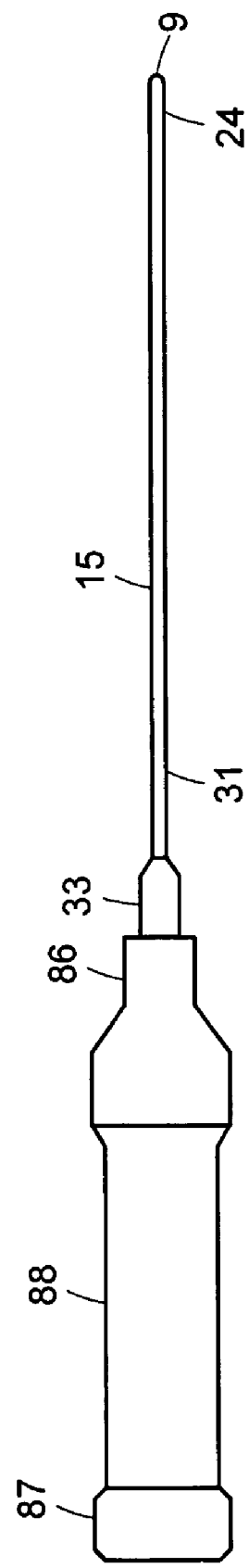
FIG. 2 is a side plan view of an ultrasonic probe of the present invention having a uniform diameter from a proximal end of the ultrasonic probe to a distal end of the ultrasonic probe.

FIG. 2 shows an alternative embodiment of the ultrasonic probe 15 of the present invention. In the embodiment of the present invention shown in FIG. 2, the diameter of the ultrasonic probe 15 is approximately uniform from the proximal end 31 of the ultrasonic probe 15 to the distal end 24 of the ultrasonic probe 15.

In a preferred embodiment of the present invention, the ultrasonic probe 15 is a wire. In a preferred embodiment of the present invention, a cross section of the ultrasonic probe is approximately circular from the proximal end 31 of the ultrasonic probe 15 to the distal end 24 of the ultrasonic probe 15. In an embodiment of the present invention, the ultrasonic probe 15 is elongated. In an embodiment of the present invention, the diameter of the ultrasonic probe 15 decreases at greater than two defined intervals. In an embodiment of the present invention, the diameter transitions 82 of the ultrasonic probe 15 are tapered to gradually change the diameter from the proximal end 31 to the distal end 24 along the longitudinal axis of the ultrasonic probe 15. In another embodiment of the present invention, the diameter transitions 82 of the ultrasonic probe 15 are stepwise to change the diameter from the proximal end 31 to the distal end 24 along the longitudinal axis of the ultrasonic probe 15. Those skilled in the art will recognize that there can be any number of defined intervals and diameter transitions, and that the diameter transitions can be of any shape known in the art and be within the spirit and scope of the present invention.

In an embodiment of the present invention, the gradual change of the diameter from the proximal end 31 to the distal end 24 occurs over the at least one diameter transitions 82, with each diameter transition 82 having an approximately equal length. In another embodiment of the present invention, the gradual change of the diameter from the proximal end 31 to the distal end 24 occurs over a plurality of diameter transitions 82 with each diameter transition 82 having a varying length. The diameter transition 82 refers to a section where the diameter varies from a first diameter to a second diameter.

The probe tip 9 can be any shape including, but not limited to, bent, a ball or larger shapes. In one embodiment of the present invention, the ultrasonic energy source 99 is a physical part of the ultrasonic medical device 11. In another embodiment of the present invention, the ultrasonic energy source 99 is not an integral part of the ultrasonic medical device 11. The ultrasonic probe 15 is used to treat a biological material and may be disposed of after use. In a preferred embodiment of the present invention, the ultrasonic probe 15 is for a single use and on a single patient. In a preferred embodiment of the present invention, the ultrasonic probe 15 is disposable. In another embodiment of the present invention, the ultrasonic probe 15 can be used multiple times.

The ultrasonic probe 15 has a stiffness that gives the ultrasonic probe 15 a flexibility allowing the ultrasonic probe 15 to be deflected and articulated when the ultrasonic medical device 11 is in motion. The ultrasonic probe 15 can be bent, flexed and deflected to reach the biological material at locations in the vasculature of the body that are difficult to reach. The ultrasonic probe 15 has a flexibility to support a torsional vibration and a transverse vibration.

In a preferred embodiment of the present invention, the ultrasonic probe 15 comprises a substantially uniform cross section from the proximal end 31 to the distal end 24. In a preferred embodiment of the present invention, a cross section of the ultrasonic probe 15 is approximately circular. In another embodiment of the present invention, a portion of the longitudinal axis of the ultrasonic probe 15 is radially asymmetric. In another embodiment of the present invention, the cross section of the ultrasonic probe 15 is spline shaped with a plurality of projections extending from an outer surface of the ultrasonic probe 15. In another embodiment of the present invention, the shape of the cross section of the ultrasonic probe 15 includes, but is not limited to, square, trapezoidal, elliptical, rectangular, oval, triangular, circular with a flat spot and similar cross sections. Those skilled in the art will recognize that other cross sectional geometries known in the art would be within the spirit and scope of the present invention.

In another embodiment of the present invention, the ultrasonic probe comprises a varying cross section from the proximal end 31 of the ultrasonic probe 15 to the distal end 24 of the ultrasonic probe 15. Various cross sectional shapes including, but not limited to square, trapezoidal, elliptical, spline shaped, rectangular, oval, triangular, circular with a flat spot and similar cross sections can be used to modify the active area.

In a preferred embodiment of the present invention, the ultrasonic probe 15 comprises titanium or a titanium alloy. In a preferred embodiment of the present invention, the ultrasonic probe 15 comprises titanium alloy Ti-6Al-4V. The elements comprising Ti-6Al-4V and the representative elemental weight percentages of Ti-6Al-4V are titanium (about 90%), aluminum (about 6%), vanadium (about 4%), iron (maximum about 0.25%) and oxygen (maximum about 0.2%). Titanium is a strong, flexible, low density, low radiopacity and easily fabricated metal that is used as a structural material. Titanium and its alloys have excellent corrosion resistance in many environments and have good elevated temperature properties. In another embodiment of the present invention, the ultrasonic probe 15 comprises stainless steel. In another embodiment of the present invention, the ultrasonic probe 15 comprises an alloy of stainless steel. In another embodiment of the present invention, the ultrasonic probe 15 comprises aluminum. In another embodiment of the present invention, the ultrasonic probe 15 comprises an alloy of aluminum. In another embodiment of the present invention, the ultrasonic probe 15 comprises a combination of titanium and stainless steel. Those skilled in the art will recognize that the ultrasonic probe can be comprised of many other materials known in the art and be within the spirit and scope of the present invention.

In a preferred embodiment of the present invention, the ultrasonic probe 15 has a small diameter. In an embodiment of the present invention, the diameter of the ultrasonic probe 15 gradually decreases from the proximal end 31 to the distal end 24. In an embodiment of the present invention, the diameter of the distal end 24 of the ultrasonic probe 15 is about 0.004 inches. In another embodiment of the present invention, the diameter of the distal end 24 of the ultrasonic probe 15 is about 0.015 inches. In other embodiments of the present invention, the diameter of the distal end 24 of the ultrasonic probe 15 varies between about 0.003 inches and about 0.025 inches. Those skilled in the art will recognize an ultrasonic probe 15 can have a diameter at the distal end 24 smaller than about 0.003 inches, larger than about 0.025 inches, and between about 0.003 inches and about 0.025 inches and be within the spirit and scope of the present invention.

In an embodiment of the present invention, the diameter of the proximal end 31 of the ultrasonic probe 15 is about 0.012 inches. In another embodiment of the present invention, the diameter of the proximal end 31 of the ultrasonic probe 15 is about 0.025 inches. In other embodiments of the present invention, the diameter of the proximal end 31 of the ultrasonic probe 15 varies between about 0.003 inches and about 0.025 inches. Those skilled in the art will recognize the ultrasonic probe 15 can have a diameter at the proximal end 31 smaller than about 0.003 inches, larger than about 0.025 inches, and between about 0.003 inches and about 0.025 inches and be within the spirit and scope of the present invention.

The length of the ultrasonic probe 15 of the present invention is chosen so as to be resonant in a torsional mode and a transverse mode. In an embodiment of the present invention, the ultrasonic probe 15 is between about 30 centimeters and about 300 centimeters in length. For the ultrasonic probe 15 to operate in the torsional mode and the transverse mode, the ultrasonic probe 15 should be detuned from the transducer, meaning that the length of the ultrasonic probe 15 should not be an integer multiple of one-half wavelength of the fundamental torsional resonance of the transducer. The ultrasonic probe 15 is detuned from the transducer when the resonant frequency of the ultrasonic probe 15 is different from the resonant frequency of the transducer. The section below entitled "Theory of Operation" provides details and equations for determining the length for the ultrasonic probe operating in the torsional mode and the transverse mode. For example, for an ultrasonic probe comprised of titanium operating at a frequency of 20 kHz, the length of the ultrasonic probe should not be an integer multiple of one-half wavelength (approximately 7.58 centimeters (about 3 inches)). Those skilled in the art will recognize an ultrasonic probe can have a length shorter than about 30 centimeters, a length longer than about 300 centimeters and a length between about 30 centimeters and about 300 centimeters and be within the spirit and scope of the present invention.

The handle 88 surrounds the transducer located between the proximal end 31 of the ultrasonic probe 15 and the connector 93. In a preferred embodiment of the present invention, the transducer includes, but is not limited to, a horn, an electrode, an insulator, a backnut, a washer, a piezo microphone, and a piezo drive. The transducer converts electrical energy provided by the ultrasonic energy source 99 to mechanical energy and sets the operating frequency of the ultrasonic medical device 11. By an appropriately oriented and driven cylindrical array of piezoelectric crystals of the transducer, the horn creates a torsional wave along at least a portion of the longitudinal axis of the ultrasonic probe 15, causing the ultrasonic probe 15 to vibrate in a torsional mode with a torsional vibration. The transducer crystals are vibrated in a direction approximately tangential to the cylindrical surface of the ultrasonic probe 15. U.S. Pat. No. 2,838,695 to Thurston describes how an appropriately oriented and driven cylindrical array of transducer crystals creates torsional waves, and the entirety of this patent is hereby incorporated herein by reference. The transducer transmits ultrasonic energy received from the ultrasonic energy source 99 to the ultrasonic probe 15, causing the ultrasonic probe 15 to vibrate in a torsional mode. The transducer is capable of engaging the ultrasonic probe 15 at the proximal end 31 with sufficient restraint to form an acoustical mass that can propagate the ultrasonic energy provided by the ultrasonic energy source 99.

The ultrasonic probe 15 is moved to a treatment site of the biological material and the ultrasonic probe 15 is placed in communication with the biological material. The ultrasonic probe 15 may be swept, twisted or rotated along the treatment site of the biological material. Those skilled in the art will recognize the ultrasonic probe can be placed in communication with the biological material in many other ways known in the art and be within the spirit and scope of the present invention.

The ultrasonic energy source 99 is activated to produce the ultrasonic energy that produces a torsional vibration of the ultrasonic probe 15. The ultrasonic energy source 99 provides the electrical power to the transducer at the resonant frequency of the transducer. The ultrasonic energy source 99 provides a low power electric signal of between about 2 watts to about 15 watts to the transducer that is located within the handle 88. Piezoelectric ceramic crystals inside the transducer create a torsional vibration that is converted into a standing torsional wave along the longitudinal axis of the ultrasonic probe 15. In a preferred embodiment of the present invention, the ultrasonic energy source 99 finds the resonant frequency of the transducer through a Phase Lock Loop (PLL) circuit.

The torsional wave is transmitted along the longitudinal axis of the ultrasonic probe 15. The torsional wave produces a component of force in a transverse direction relative to the longitudinal axis of the ultrasonic probe 15, thereby exciting a transverse wave along the longitudinal axis of the ultrasonic probe 15. As a result, the ultrasonic probe 15 undergoes both a torsional vibration and a transverse vibration.

The torsional vibration along the longitudinal axis of the ultrasonic probe 15 induces a transverse vibration along an active area of the ultrasonic probe 15. In a preferred embodiment of the present invention, the active area is at least a portion of the longitudinal axis of the ultrasonic probe 15. In an embodiment of the present invention, the active area is at the distal end 24 of the ultrasonic probe 15. Those skilled in the art will recognize the active area can be located anywhere along the longitudinal axis of the ultrasonic probe and the active area can have varying lengths and be within the spirit and scope of the present invention.

Figure 3:
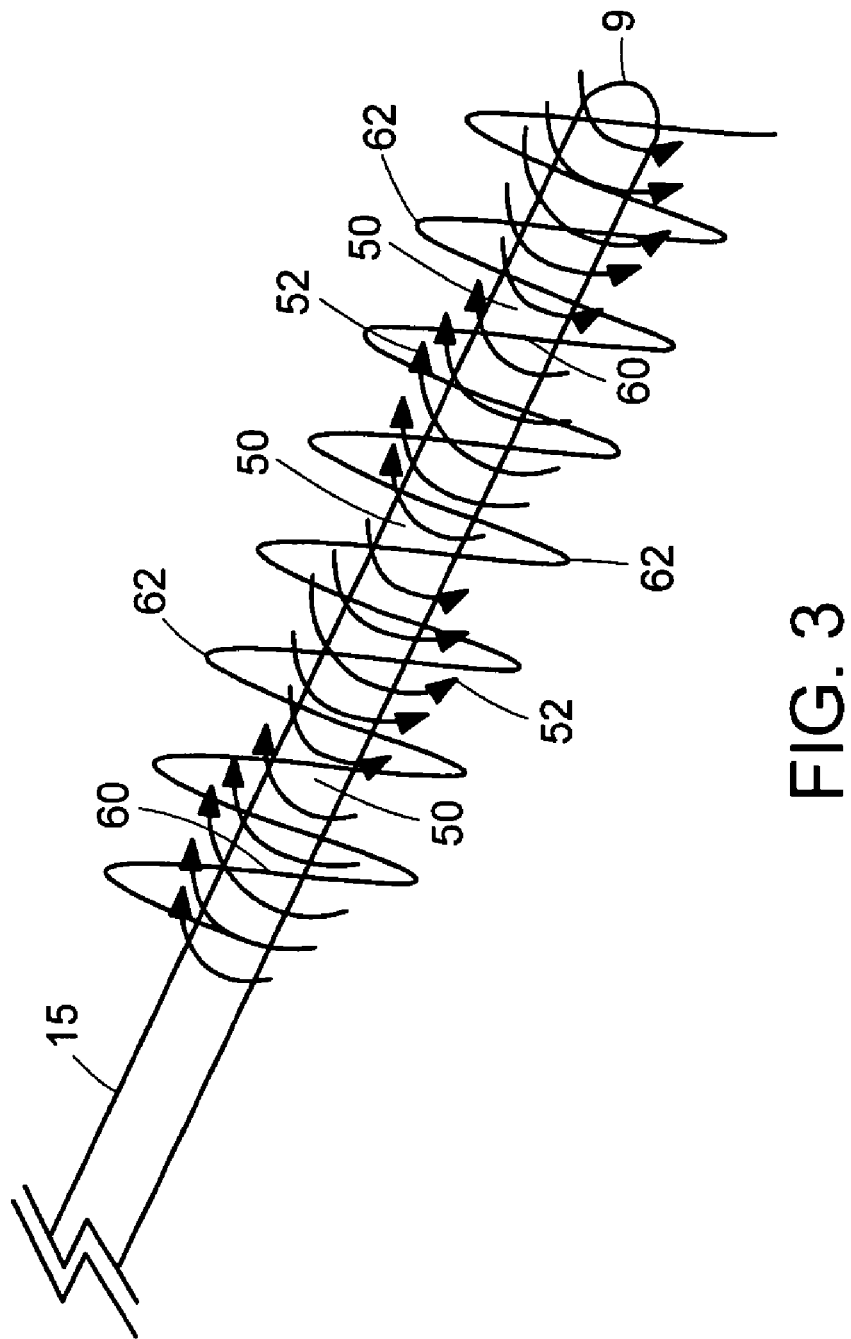
FIG. 3 is a fragmentary perspective view of an ultrasonic probe of the present invention having a torsional vibration and a transverse vibration along an active area of the ultrasonic probe.

FIG. 3 shows a perspective view of the ultrasonic probe 15 of the present invention undergoing a torsional vibration and a transverse vibration along the active area of the ultrasonic probe 15. The torsional vibration is shown as the alternating clockwise and counterclockwise sets of arrows, with each set comprising five arrows in FIG. 3. The transverse vibration is shown with a wave-like motion in a repeating form where the vibration rises from the longitudinal axis to a maximum amplitude, descends back down to the longitudinal axis to a minimum amplitude, proceeds from the longitudinal axis to a maximum amplitude and returns to the longitudinal axis of the ultrasonic probe 15.

Depending upon physical properties (i.e. length, diameter, etc.) and material properties (i.e., yield strength, modulus, etc.) of the ultrasonic probe 15, the transverse vibration is excited by the torsional vibration. The active area of the ultrasonic probe 15 undergoes both the torsional vibration and the transverse vibration. By vibrating the ultrasonic probe 15 both torsionally and transversely, the ultrasonic probe 15 is operated in a torsional mode of vibration and a transverse mode of vibration. Coupling of the torsional mode of vibration and the transverse mode of vibration is possible because of common shear components for the elastic forces. The transverse vibration is induced when the frequency of the transducer is close to a transverse resonant frequency of the ultrasonic probe 15. The combination of the torsional mode of vibration and the transverse mode of vibration is possible because for each torsional mode of vibration, there are many close transverse modes of vibration.

The torsional wave motion along the longitudinal axis of the ultrasonic probe 15 creates a shear force gradient along the longitudinal axis of the ultrasonic probe 15. The shear force gradient generates a transverse motion when the frequency of the torsional motion is close to a transverse resonant frequency of the ultrasonic probe 15. The shear force is in the approximate same direction as the transverse motion. The magnitude of the shear force is proportional to the torsional or angular displacement. As shown in FIG. 3, the wavelength for the transverse mode of vibration is less than the wavelength for the torsional mode of vibration. In an embodiment of the present invention, two or more wavelengths for the transverse mode of vibration are produced for one wavelength for the torsional mode of vibration. In the embodiment of the present invention shown in FIG. 3, the transverse vibration wavelength is about one-fifth (⅕) of the torsional vibration wavelength.

By applying tension to the ultrasonic probe 15, the transverse and torsional vibrations are shifted in frequency. For example, bending the ultrasonic probe 15 causes the transverse and torsional vibration to shift in frequency. Bending the ultrasonic probe 15 causes a shift in frequency resulting from the changes in tension. In an embodiment of the present invention, the ultrasonic probe 15 is coupled to the transducer through an acoustic impedance mismatch so that the tuning of the ultrasonic probe 15 will not affect the drive frequency. The acoustic impedance mismatch can be achieved by maintaining a large difference between the moment of inertia of the transducer and the moment of inertia of the ultrasonic probe 15. The acoustic impedance mismatch can be created by a discontinuity at the transducer or created further down the longitudinal axis of the ultrasonic probe 15 by reducing the diameter in a stepwise manner toward the distal end 24 of the ultrasonic probe 15. An ultrasonic probe device having an impedance mismatch with rapid attachment and detachment means is described in Assignee's co-pending patent application U.S. Ser. No. 10/268,487, the entirety of which is hereby incorporated herein by reference.

Figure 4:
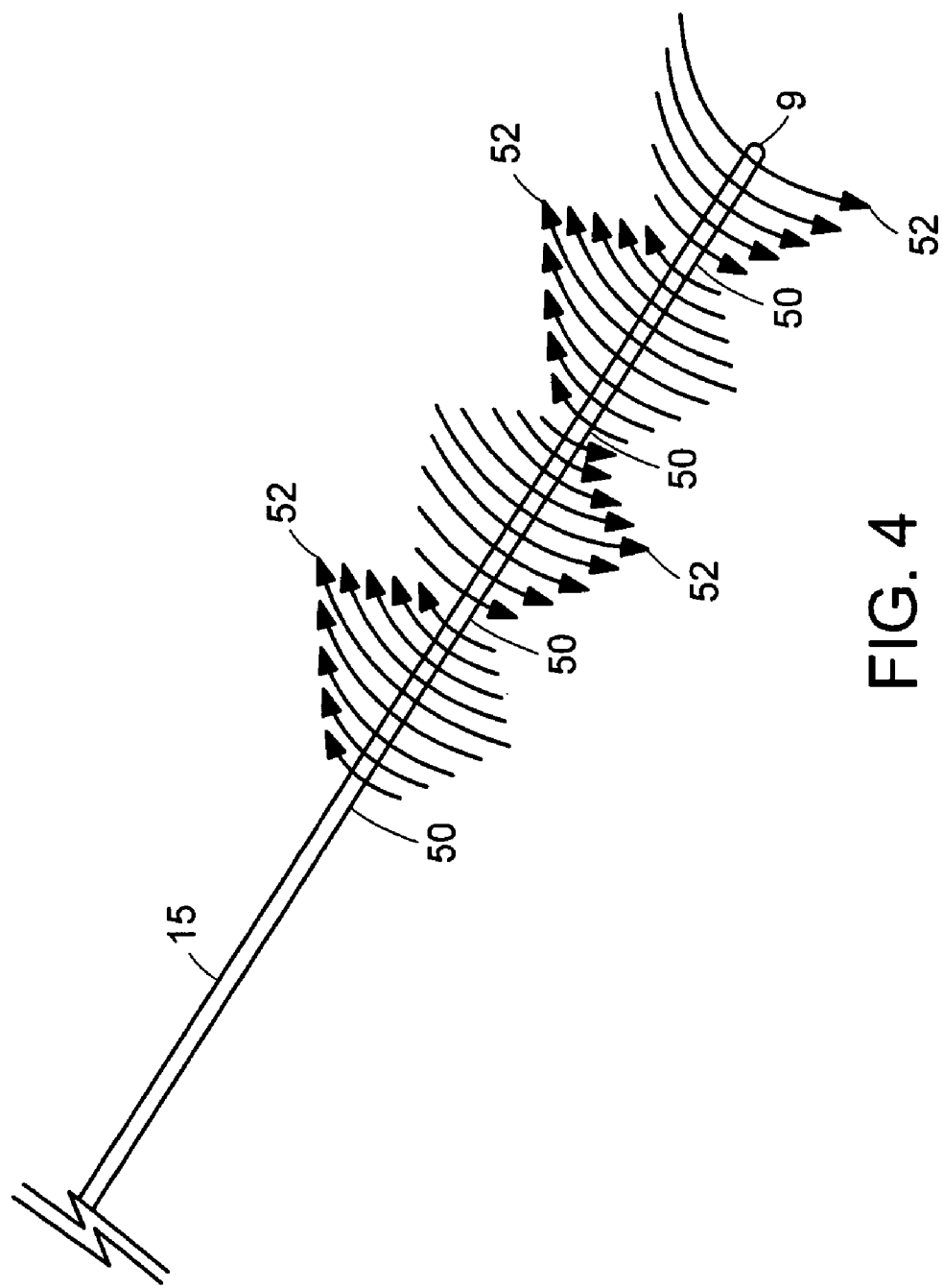
FIG. 4 is a fragmentary perspective view of the ultrasonic probe of the present invention undergoing a torsional vibration.
Figure 5A:
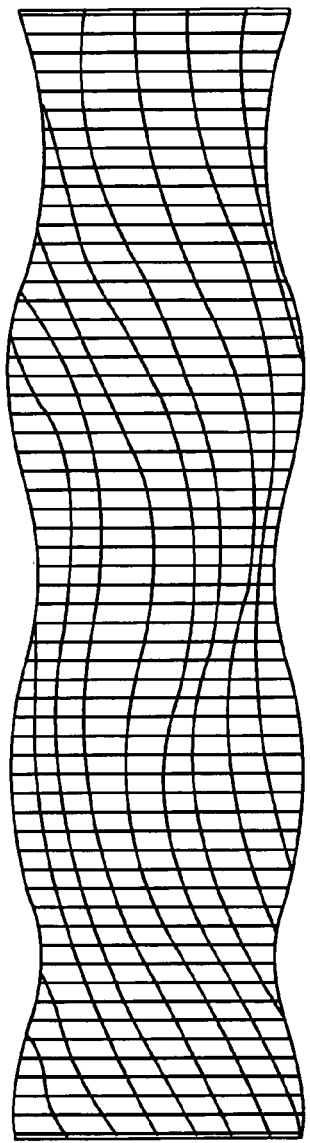
FIG. 5A is a fragmentary side plan view of the ultrasonic probe of the present invention undergoing a torsional vibration.
Figure 5B:
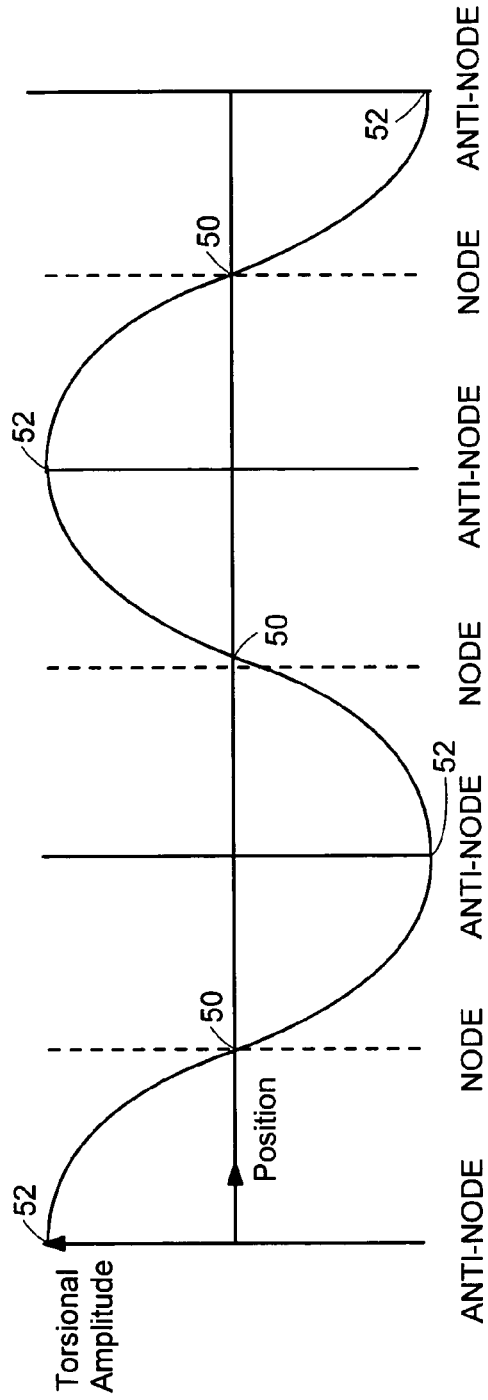
FIG. 5B is a graph corresponding to the torsional vibration shown in FIG. 5A
Figure 6:
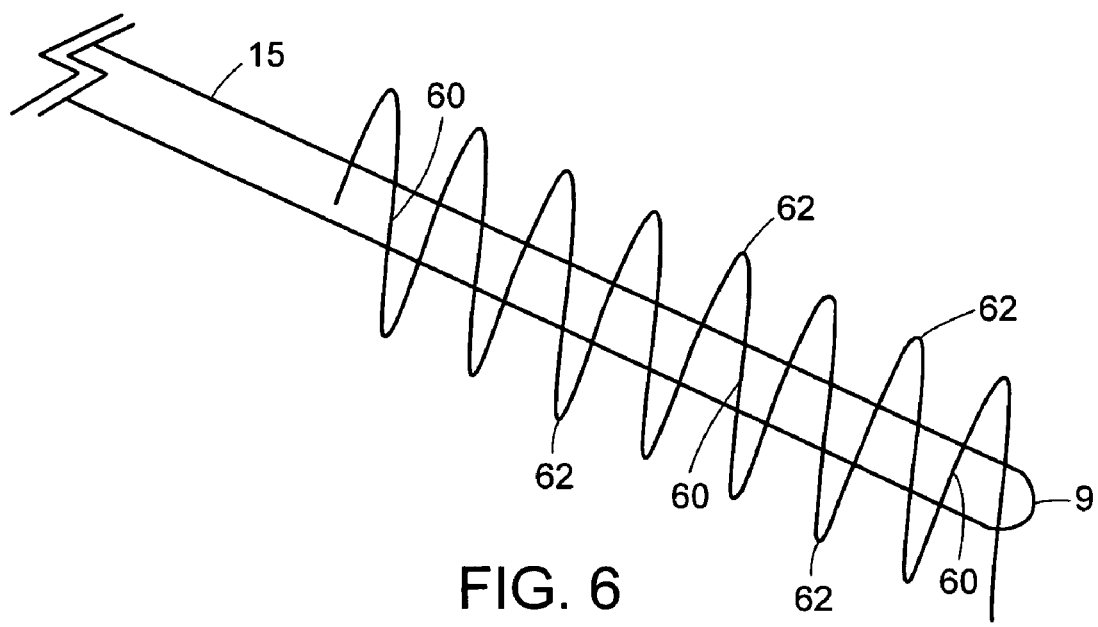
FIG. 6 is a fragmentary side plan view of the ultrasonic probe of the present invention undergoing a transverse vibration.

FIG. 4 shows a fragmentary perspective view of the ultrasonic probe 15 of the present invention undergoing the torsional vibration. As discussed above, the alternating clockwise and counterclockwise arrows represent the torsional vibration, showing the rotational and counterrotational motion of the ultrasonic probe 15. FIG. 5A shows a fragmentary side plan view of the ultrasonic probe 15 of the present invention undergoing the torsional vibration while FIG. 5B shows a graph corresponding to the torsional vibration shown in FIG. 5A. FIG. 6 shows the ultrasonic probe 15 undergoing the transverse vibration. To clearly describe the torsional vibration and the transverse vibration, the torsional vibration will be examined while discussing FIG. 4, FIG. 5A and FIG. 5B while the transverse vibration will be separately examined while discussing FIG. 6.

The torsional vibration of the ultrasonic probe 15 in FIG. 4 and FIG. 5A is shown as movement of the ultrasonic probe in alternating clockwise and counterclockwise directions along the longitudinal axis of the ultrasonic probe 15. The torsional vibration shown in FIG. 4 and FIG. 5A is a torsional oscillation whereby equally spaced points along the longitudinal axis of the ultrasonic probe 15 including the probe tip 9 vibrate back and forth in a short arc of the same amplitude in a plane perpendicular to the longitudinal axis of the ultrasonic probe 15. The vibration creates a plurality of torsional nodes 50 and a plurality of torsional anti-nodes 52 along art active area of the ultrasonic probe 15. A section proximal to each of the plurality of torsional nodes 50 and a section distal to each of the plurality of torsional nodes 50 are vibrated out of phase, with the proximal section vibrated in a clockwise direction and the distal section vibrated in a counterclockwise direction, or vice versa. The torsional vibration produces a rotation and counterrotation along the longitudinal axis of the ultrasonic probe 15. As shown in FIG. 5A and FIG. 5B, the torsional vibration is propagated in a forward direction and a reverse direction about a torsional node 50. Traveling along the longitudinal axis, at each torsional node 50, the direction of the rotation reverses and the amplitude increases until reaching a torsional anti node 52 and subsequently decreases toward the next torsional node 50. An ultrasonic probe operating in a torsional mode is biological material ablation are described in the Assignee's co-pending patent application U.S. Ser. No. 10/774,985, filed Feb. 9, 2004, and the entirety of this application is hereby incorporated herein by reference.

FIG. 5A shows the alternating clockwise and counterclockwise motion about the torsional node 50 and shows an expansion and a compression of the ultrasonic probe 15 in the torsional mode. FIG. 5A shows the expansion of the ultrasonic probe 15 as the clockwise and counterclockwise motion of the ultrasonic probe 15 extends away from the torsional node 50. As the alternating clockwise and counterclockwise motion returns back to the torsional node 50, the ultrasonic probe 15 is compressed. The ultrasonic probe 15 will expand and compress about the plurality of torsional nodes 50 along an active area of the ultrasonic probe 15.

The transverse vibration of the ultrasonic probe 15 shown in FIG. 6 results in a portion of the longitudinal axis of the ultrasonic probe 15 vibrated in a direction not parallel to the longitudinal axis of the ultrasonic probe 15. The transverse vibration results in movement of the longitudinal axis of the ultrasonic probe 15 in a direction approximately perpendicular to the longitudinal axis of the ultrasonic probe 15. The transverse vibration creates a plurality of transverse nodes 60 and a plurality of transverse anti-nodes 62 along the active area of the ultrasonic probe 15. Transversely vibrating ultrasonic probes for biological material ablation are described in the Assignee's U.S. Pat. Nos. 6,551,337 and 6,652,547 and co-pending patent application U.S. Ser. No. 09/917,471, which further describe the design parameters for such an ultrasonic probe and its use in ultrasonic devices for an ablation, and the entirety of these patents and patent applications are hereby incorporated herein by reference.

As best shown in FIG. 3, the torsional vibration shown in FIG. 4 and the transverse vibration shown in FIG. 6 are combined at the active area of the ultrasonic probe 15 to produce the torsional vibration and transverse vibration shown in FIG. 3. The torsional vibration and the transverse vibration create a plurality of nodes 50, 60 and a plurality of anti-nodes 52, 62 along the active area of the ultrasonic probe 15. In the torsional mode of vibration and the transverse mode of vibration, the active area of the ultrasonic probe 15 is vibrated in a direction not parallel to the longitudinal axis of the ultrasonic probe 15 while equally spaced points along the longitudinal axis of the ultrasonic probe 15 in a proximal section vibrate back and forth in a short arc about the longitudinal axis of the ultrasonic probe 15. In a preferred embodiment of the present invention, the torsional vibration and the transverse vibration are superimposed over the active area of the ultrasonic probe 15 (FIG. 3).

Figure 7:
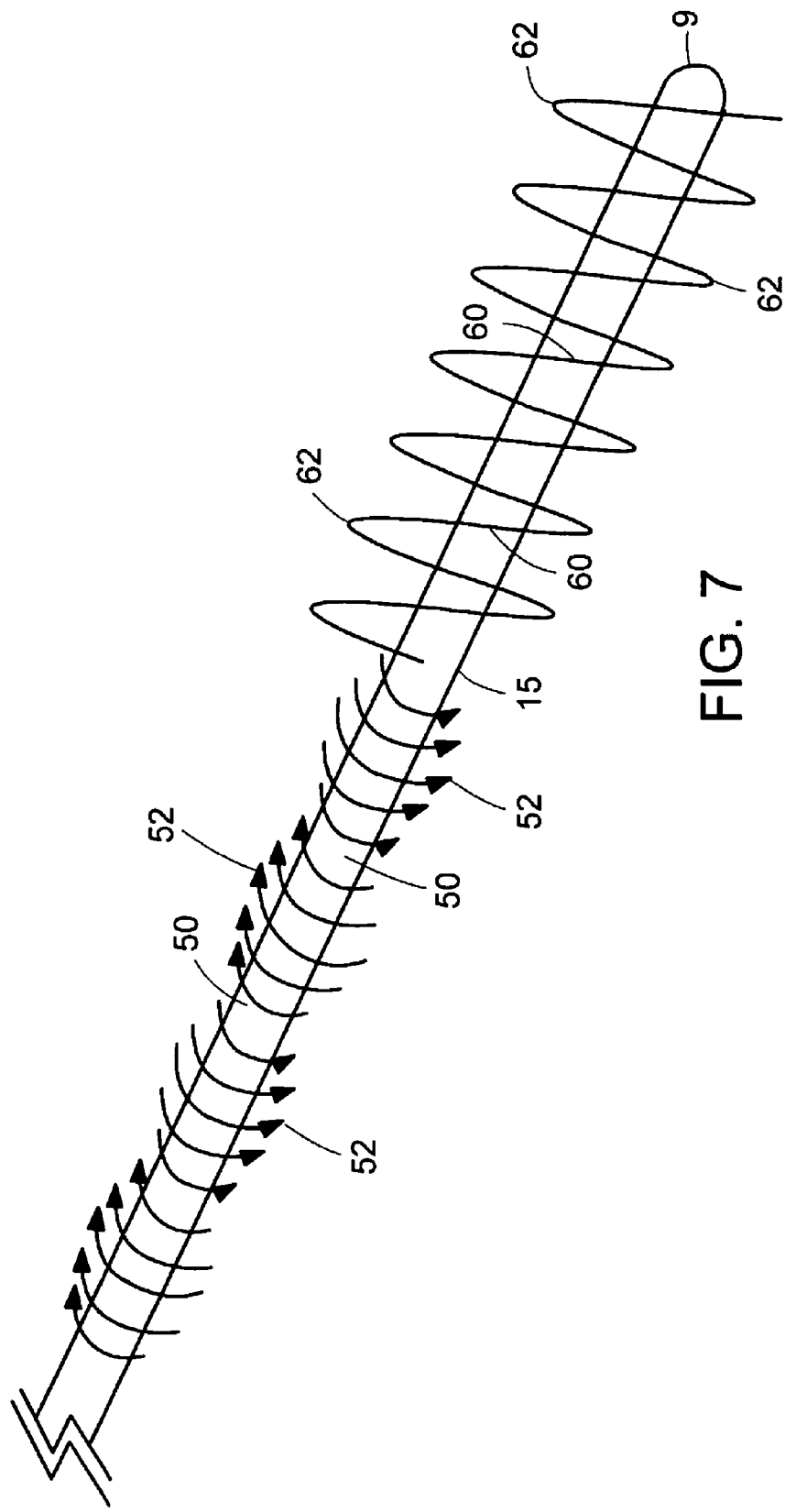
FIG. 7 is a fragmentary perspective view of the ultrasonic probe of the present invention undergoing a transverse vibration along an active area of the ultrasonic probe and a torsional vibration along a section proximal to the active area of the ultrasonic probe.

In an alternative embodiment of the present invention shown in FIG. 7, the torsional vibration of the ultrasonic probe 15 creates the transverse vibration along an active area of the ultrasonic probe, where the active area undergoes the transverse vibration without the torsional vibration. The transverse vibration creates the plurality of transverse nodes 60 and the plurality of transverse anti-nodes 62 along the longitudinal axis of the ultrasonic probe 15. FIG. 7 shows the alternative embodiment wherein the torsional vibration and the transverse vibration are segregated over the longitudinal axis of the ultrasonic probe 15. In one embodiment, a segregation section of the ultrasonic probe 15 is between the torsional vibration and the transverse vibration. In another embodiment, there is a minor overlap of the torsional vibration and the transverse vibration over the active area of the ultrasonic probe 15. Those skilled in the art will recognize a length of the segregation section between the torsional vibration and the transverse vibration can vary and be within the spirit and scope of the present invention.

Figure 8:
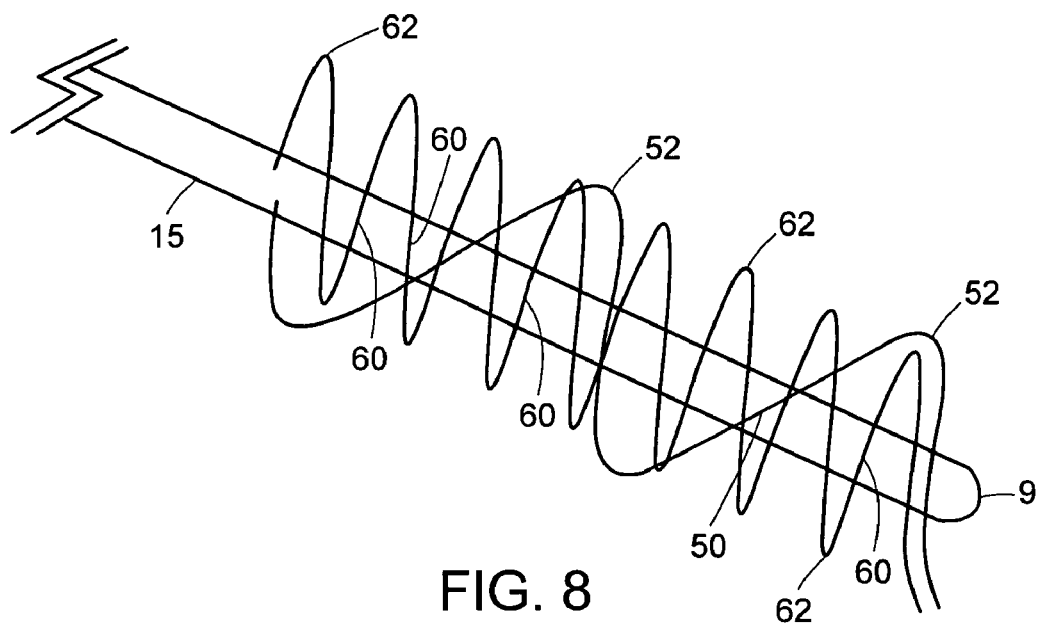
FIG. 8 is a fragmentary side plan view of the ultrasonic probe of the present invention having a plurality of nodes and a plurality of anti-nodes along an active area of the ultrasonic probe.
Figure 9:
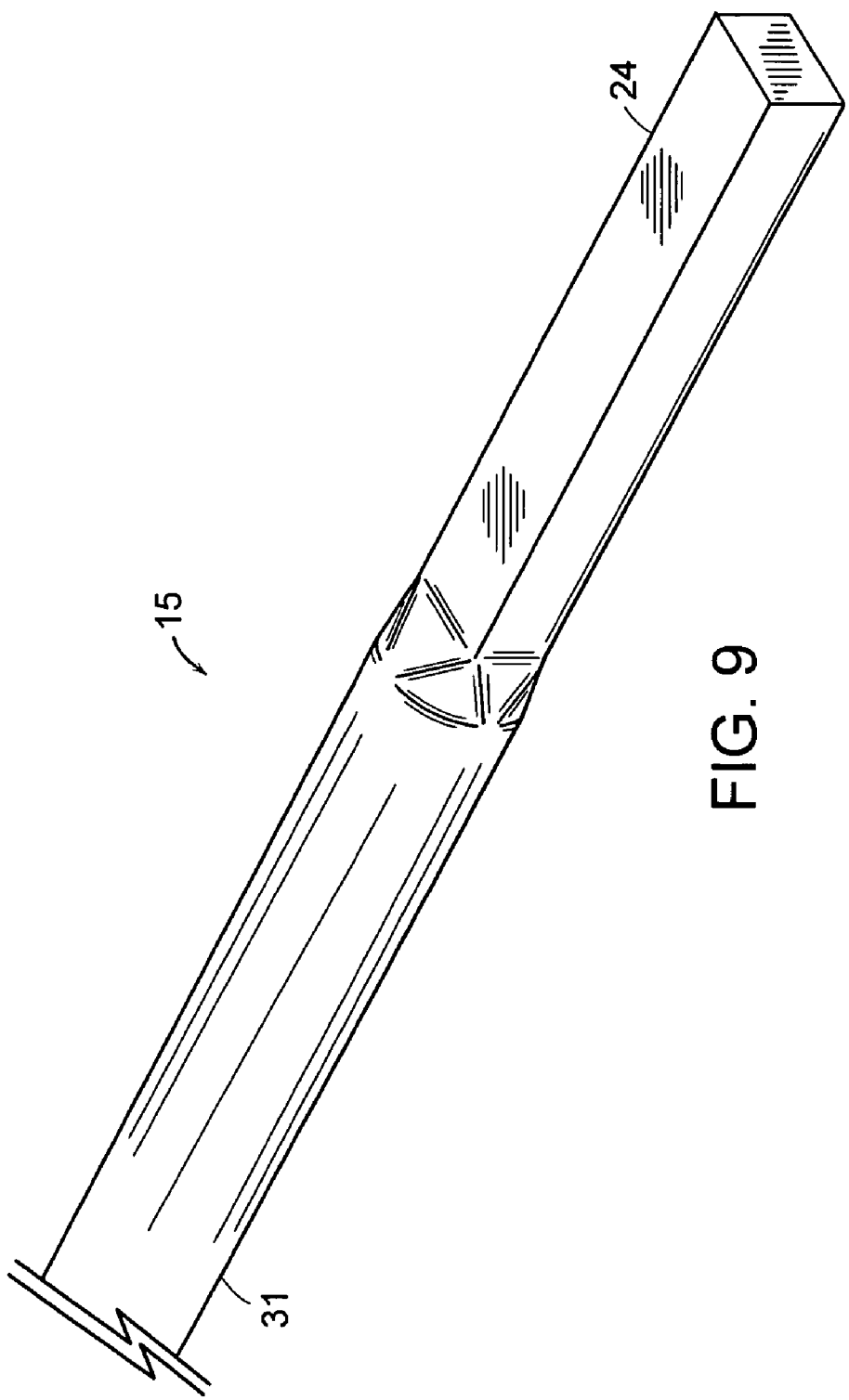
FIG. 9 is a fragmentary perspective view of a portion of a longitudinal axis of an ultrasonic probe of the present invention comprising an approximately circular cross section at a proximal end of the ultrasonic probe and a radially asymmetric cross section at a distal end of the ultrasonic probe.

FIG. 8 shows a fragmentary perspective view of the ultrasonic probe 15 with the plurality of nodes 50, 60 and the plurality of anti-nodes 52, 62 for the torsional mode of vibration and the transverse mode of vibration along the active area of the ultrasonic probe 15 caused by the torsional vibration and the transverse vibration of the ultrasonic probe 15. FIG. 8 and FIG. 3 both show the pattern of the plurality of nodes 50, 60, and the plurality of anti-nodes 52, 62 for the torsional mode of vibration and the transverse mode of vibration are independently created for each mode of vibration. As a result, the pattern of the plurality of nodes 50, 60 and the plurality of anti-nodes 52, 62 has a different spacing for the torsional mode of vibration and the transverse mode of vibration. The plurality of nodes 50, 60 are areas of minimum energy and minimum vibration. The plurality of anti-nodes 52, 62, areas of maximum energy and maximum vibration, also occur at repeating intervals along the active area of the ultrasonic probe 15. The torsional vibration and the transverse vibration at the active area of the ultrasonic probe 15 create the plurality of nodes 50, 60 and the plurality of anti-nodes 52, 62 along the active area of the ultrasonic probe 15 resulting in cavitation in a medium surrounding the ultrasonic probe 15 that ablates the biological material.

The combined torsional motion and transverse motion of the ultrasonic probe 15 caused by the torsional vibration and the transverse vibration causes an interaction between the surface of the ultrasonic probe 15 and the medium surrounding the ultrasonic probe 15 to cause an acoustic wave in the medium surrounding the ultrasonic probe 15. In effect, acoustic energy is generated in the medium surrounding the ultrasonic probe 15. The motion caused by the torsional vibration and the transverse vibration causes cavitation in the medium surrounding the ultrasonic probe 15 over an active area of the ultrasonic probe 15.

Cavitation is a process in which small voids are formed in a surrounding fluid through the rapid motion of the ultrasonic probe 15 and the voids are subsequently forced to compress. The compression of the voids creates a wave of acoustic energy which acts to dissolve the matrix binding the biological material, while having no damaging effects on healthy tissue. The biological material is resolved into a particulate having a size on the order of red blood cells (approximately 5 microns in diameter). The size of the particulate is such that the particulate is easily discharged from the body through conventional methods or simply dissolves into the blood stream. A conventional method of discharging the particulate from the body includes transferring the particulate through the blood stream to the kidney where the particulate is excreted as bodily waste.

The torsional motion of the ultrasonic probe 15 is less than the transverse motion of the ultrasonic probe 15. Once the transverse motion is established on the ultrasonic probe 15, almost all additional energy goes into transverse motion and the amplitude of the torsional motion does not increase appreciably past this point. Cavitation is created primarily because of the transverse motion of the ultrasonic probe 15.

The number of nodes 50, 60 and the number of anti-nodes 52, 62 occurring along the active area of the ultrasonic probe 15 is modulated by changing the frequency of energy supplied by the ultrasonic energy source 99. The exact frequency, however, is not critical and the ultrasonic energy source 99 run at, for example, about 20 kHz is sufficient to create an effective number of biological material destroying anti-nodes 52, 62 along the longitudinal axis of the ultrasonic probe 15. The low frequency requirement of the present invention is a further advantage in that the low frequency requirement leads to less damage to healthy tissue. Those skilled in the art will recognize that changing the dimensions of the ultrasonic probe 15, including diameter, length and distance to the ultrasonic energy source 99, will affect the number and spacing of the nodes 50, 60 and the anti-nodes 52, 62 along the active area of the ultrasonic probe 15.

The present invention allows the use of ultrasonic energy to be applied to the biological material selectively, because the ultrasonic probe 15 conducts energy across a frequency range from about 10 kHz through about 100 kHz. The amount of ultrasonic energy to be applied to a particular treatment site is a function of the amplitude and frequency of vibration of the ultrasonic probe 15. In general, the amplitude or throw rate of energy is in the range of about 25 microns to about 250 microns, and the frequency in the range of about 10 kHz to about 100 kHz. In a preferred embodiment of the present invention, the frequency of ultrasonic energy is from about 20 kHz to about 35 kHz.

As discussed above, once the transverse motion of the ultrasonic probe 15 is established, almost all additional energy goes into transverse motion of the ultrasonic probe 15 and the amplitude of the torsional motion does not increase appreciably past this point. As such, in the preferred embodiment of the present invention, the torsional motion of the ultrasonic probe 15 is less than the transverse motion of the ultrasonic probe 15.

FIG. 9 shows a perspective view of another embodiment of the present invention where the cross section of the ultrasonic probe 15 varies from the proximal end 31 of the ultrasonic probe 15 to the distal end 24 of the ultrasonic probe 15. In the embodiment of the present invention shown in FIG. 9, the cross section of the ultrasonic probe varies from an approximately circular cross at the proximal end 31 of the ultrasonic probe 15 to a radially asymmetric cross section at the distal end 24 of the ultrasonic probe 15. In FIG. 9, the radially asymmetric cross section at the distal end 24 of the ultrasonic probe 15 is approximately rectangular. Other radially asymmetric cross sections at the distal end 24 of the ultrasonic probe 15 that can be used to create torsional motion that subsequently produces cavitation along a portion of the length of the longitudinal axis include, but are not limited to, square, trapezoidal, elliptical, star shaped, rectangular, oval, triangular, circular with a flat spot and similar cross sections. Those skilled in the art will recognize other radially asymmetric cross sections known in the art are within the spirit and scope of the present invention.

The torsional vibration and the transverse vibration of the ultrasonic probe 15 according to the present invention differ from an axial (or longitudinal) mode of vibration disclosed in the prior art. Rather than vibrating in an axial direction, the ultrasonic probe 15 of the present invention vibrates both torsionally and transversely along the active area of the ultrasonic probe 15. As a consequence of the torsional vibration and the transverse vibration of the ultrasonic probe 15, the biological material destroying effects of the ultrasonic medical device 11 are not limited to the tip of the ultrasonic probe 15. Rather, as a section of the longitudinal axis of the ultrasonic probe 15 is positioned in proximity to the biological material, the biological material is removed in all areas adjacent to the plurality of nodes 50, 60 and the plurality of anti-nodes 52, 62 that are produced by the torsional vibration and transverse vibration along the active area of the ultrasonic probe 15, typically in a region having a radius of up to about 6 mm around the ultrasonic probe 15. The torsional mode of vibration and transverse mode of vibration results in an ultrasonic energy transfer to the biological material with minimal loss of ultrasonic energy that could limit the effectiveness of the ultrasonic medical device 11. In addition to increasing the biological material destroying area of the ultrasonic probe 15, the probe tip 9 is able to ablate the biological material when the probe tip 9 encounters the biological material and the ultrasonic probe 15 is vibrated torsionally and transversely.

In one embodiment of the present invention, the ultrasonic probe 15 is swept along the treatment site of the biological material. In another embodiment of the present invention, the ultrasonic probe 15 is moved back and forth along the treatment site of the biological material. In another embodiment of the present invention, the ultrasonic probe 15 is twisted along the treatment site of the biological material. In another embodiment of the present invention, the ultrasonic probe 15 is rotated along the treatment site of the biological material. Those skilled in the art will recognize the ultrasonic probe can be place in communication with the biological material in many ways known in the art and be within the spirit and scope of the present invention.

Unlike the prior art longitudinal mode of operation where the biological material destroying effects are limited to the tip of the probe, an active area of the ultrasonic probe 15 operating in the torsional mode and transverse mode extends from the probe tip 9 and along a portion of a longitudinal axis of the ultrasonic probe 15. The section below entitled "Theory of Operation" discusses some differences between the longitudinal mode of operation used in the prior art and the torsional mode and transverse mode of operation used in the present invention. In the torsional mode and transverse mode of vibration, the biological material is removed in all areas adjacent to the plurality of nodes 50, 60 and the plurality of anti-nodes 52, 62 that are produced by the torsional vibration and transverse vibration along the active area of the ultrasonic probe 15. By treating a larger area of the treatment site of the biological material, the ultrasonic medical device 11 of the present invention allows for shorter medical procedures. By reducing the time of the medical procedure, a patient is not subjected to additional health risks associated with longer medical procedures.

Figure 10:
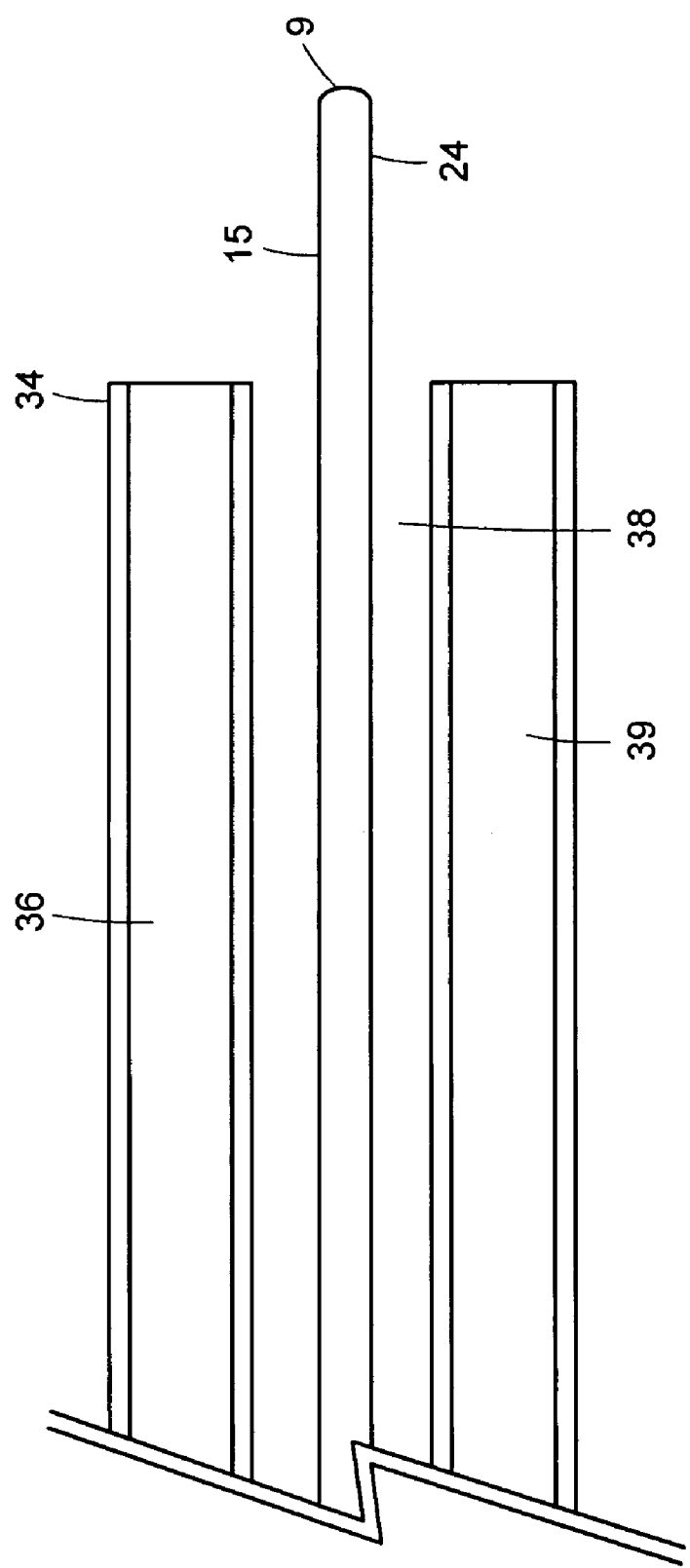
FIG. 10 is a side plan view of the ultrasonic probe of the present invention located within a sheath.

FIG. 10 shows the ultrasonic probe 15 of the present invention extending from a distal end 34 of a sheath 36. As shown in FIG. 10, the ultrasonic probe 15 is placed within the sheath 36, which can provide an at least one irrigation channel 38 and an at least one aspiration channel 39. In an embodiment of the present invention, irrigation is provided between the ultrasonic probe 15 and the sheath 36. The ultrasonic probe 15 may be moved in an axial direction within the sheath 36 to move the distal end 24 of the ultrasonic probe 15 axially inwardly and outwardly relative to the distal end 34 of the sheath 36. By extending or retracting the ultrasonic probe 15 relative to the sheath 36, the amount of the ultrasonic probe 15 exposed is modified, thereby modifying the biological material destroying area of the ultrasonic probe 15.

In an embodiment of the present invention, the sheath 36 is comprised of polytetrafluoroethylene (PTFE). In another embodiment of the present invention, the sheath 36 is comprised of teflon tubing or similar fluoropolymer tubing. The sheath absorbs the ultrasonic energy emanating from the portions of the ultrasonic probe 15 located within the sheath 36, thereby allowing control over the amount of biological material affected by the ultrasonic probe 15. The sheath 36 is preferably comprised of a material which is resistant to heat from the ultrasonic energy, even though the irrigation fluid can act as a coolant for the sheath 36.

The present invention provides a method of treating a biological material in the body with the ultrasonic medical device 11. The ultrasonic probe 15 of the ultrasonic medical device 11 is moved to the treatment site of the biological material and placed in communication with the biological material. The ultrasonic energy source 99 of the ultrasonic medical device 11 engaged to the ultrasonic probe 15 is activated to produce the torsional vibration of the ultrasonic probe 15. The transducer engaging the ultrasonic energy source 99 at the proximal end of the transducer and the ultrasonic probe 15 at the distal end of the transducer creates the torsional vibration along the longitudinal axis of the ultrasonic probe 15. The torsional vibration of the ultrasonic probe 15 induces the transverse vibration in the active area of the ultrasonic probe, wherein the active area of the ultrasonic probe 15 supports the torsional vibration and the transverse vibration.

The present invention also provides a method of removing a biological material in the body. The ultrasonic probe 15 of the ultrasonic medical device 11 is moved in the body and placed in communication with the biological material. The ultrasonic energy source 99 of the ultrasonic medical device 11 produces an electric signal that drives the transducer of the ultrasonic medical device 11 to produce a torsional vibration of the ultrasonic probe 15. The torsional vibration of the ultrasonic probe 15 induces the transverse vibration along the longitudinal axis of the ultrasonic probe 15, creating a plurality of nodes 50, 60 and a plurality of anti-nodes 52, 62 along an active area of the ultrasonic probe 15.

Theory of Operation

The torsional mode of vibration and transverse mode of vibration of the present invention differs from longitudinal mode of vibration of the prior art. In the longitudinal vibration of the prior art, the frequencies of the individual modes depend on the modulus of elasticity E and the density $\rho$.

$$c_l = \sqrt{\frac{E}{\rho}}$$

For the torsional waves, the expression is the same except the shear modulus, G, is used instead of the modulus of elasticity, E. The shear modulus, G, and the modulus of elasticity, E, are linked through Poisson's ratio $\upsilon$:

$$G = \frac{E}{2(1+\upsilon)}$$

and the corresponding torsional speed of propagation is:

$$c_t = \sqrt{\frac{GK_T}{\rho I}}$$

where $K_T$ is the torsional stiffness factor of the cross section and I is the moment of inertia of the cross section. For a circular cross section the ratio $K_T/I=1$, while for radially asymmetric cross sections the ratio $K_T/I<1$. Therefore, the speed of propagation will be slower for the torsional wave by a factor of:

$$\frac{c_t}{c_l} = \sqrt{\frac{K_T}{2(1+\upsilon)I}}$$

For a symmetric cross section $K_T/I=1$, and for a radially asymmetric cross section $K_T/I<1$. For common metals, Poisson's ratio $\upsilon$ is on the order of 0.3, therefore the speed of propagation for a torsional wave will be approximately 62% or less of that for the longitudinal wave. A decrease in the speed of propagation implies a proportional decrease in the wavelength for a given frequency. Decreasing the wavelength greatly improves the devices ability to deliver energy through the tortuous paths and the tight bends of the vasculature.

The operating frequencies of the longitudinal and torsional modes are dependent on the properties of the ultrasonic probe. Selection of material properties depends primarily on acoustic loss, the choice of operating frequency and the desired amplitude of vibration. As discussed previously, with the ultrasonic probe comprised of titanium and operating at a frequency of about 20 kHz, the torsional wave speed for a circular cross section is as follows:

$$c_t = \sqrt{\frac{\frac{E}{2(1+\nu)}}{\rho}} = \sqrt{\frac{\frac{1.1 \times 10^{11} \text{ Pa}}{2(1+0.3)}}{4600 \text{ kg/m}^3}} = 3032 \text{ m/s}$$

Using the torsional wave speed to solve for a condition of the length of the ultrasonic probe to operate in a torsional mode and a transverse mode gives:

$$L = \frac{\lambda}{2} = \frac{c}{2f} = \frac{3032 \text{ m/s}}{2(20,000 \text{ Hz})} = 0.0758 \text{ m} = 7.58 \text{ cm} \approx 3 \text{ in.}$$

Thus, for the ultrasonic probe to operate in a torsional mode and a transverse mode, the length of the ultrasonic probe should not be an integer multiple of 7.58 cm (about 3 inches) for this particular case. Those skilled in the art will recognize that changes to other material properties can influence the operation in the torsional mode and these changes are within the spirit and scope of the present invention.

The present invention provides an apparatus and a method for an ultrasonic medical device operating in a torsional mode and a transverse mode. The active area of the ultrasonic probe is vibrated in a direction not parallel to the longitudinal axis of the ultrasonic probe while equally spaced points along the active area are vibrated back and forth in a short arc along the active area of the ultrasonic probe. The present invention provides an ultrasonic medical device that is simple, user-friendly, time efficient, reliable and cost effective.

All patents, patent applications, and published references cited herein are hereby incorporated herein by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. A method comprising:
   moving an ultrasonic probe to a treatment site in a body such that the ultrasonic probe is in communication with a biological material;
   producing a torsional vibration along the ultrasonic probe, the torsional vibration inducing a transverse vibration in a portion of the ultrasonic probe; and
   tuning the transverse vibration into coincidence with the torsional vibration along the portion of the ultrasonic probe in which the transverse vibration is induced.

2. The method of claim 1 wherein the portion of the ultrasonic probe in which the transverse vibration is induced supports the torsional vibration and the transverse vibration.

3. The method of claim 1 further comprising superimposing the torsional vibration and the transverse vibration along the portion of the ultrasonic probe in which the transverse vibration is induced.

4. The method of claim 1 further comprising segregating the torsional vibration and the transverse vibration along the ultrasonic probe.

5. The method of claim 1 wherein the torsional vibration is produced by a transducer coupled to the ultrasonic probe.

6. The method of claim 1 further comprising generating acoustic energy in a medium surrounding the ultrasonic probe through an interaction of a surface of the ultrasonic probe and the medium surrounding the ultrasonic probe resulting from the torsional vibration and the transverse vibration.

7. The method of claim 1 further comprising producing a plurality of nodes and a plurality of anti-nodes along at least the portion of the ultrasonic probe in which the transverse vibration is induced.

8. The method of claim 1 further comprising producing a plurality of transverse nodes and a plurality of transverse anti-nodes along at least the portion of the ultrasonic probe in which the transverse vibration is induced.

9. The method of claim 1 further comprising producing a rotation and counterrotation of the ultrasonic probe along at least the portion of the ultrasonic probe in which the transverse vibration is induced.

10. The method of claim 1 further comprising projecting the torsional vibration in a forward direction and a reverse direction about a plurality of nodes of the ultrasonic probe.

11. The method of claim 1 further comprising sweeping the ultrasonic probe along the treatment site.

12. The method of claim 1 further comprising moving the ultrasonic probe back and forth along the treatment site.

13. The method of claim 1 further comprising rotating the ultrasonic probe along the treatment site.

14. The method of claim 1 further comprising delivering ultrasonic energy to the ultrasonic probe in a frequency range from about 10 kHz to about 100 kHz.

15. The method of claim 1 further comprising determining a resonant frequency of the transducer and providing electrical energy to a transducer at the resonant frequency of the transducer.

16. The method of claim 1 further comprising providing the ultrasonic probe having a flexibility allowing the ultrasonic probe to support the torsional vibration and the transverse vibration.

17. The method of claim 1 wherein the portion in which the transverse vibration is induced extends along at least a portion of the longitudinal axis of the ultrasonic probe.

18. The method of claim 1 wherein the ultrasonic probe has a first region having a first diameter and a second region having a second diameter, wherein the second diameter is smaller than the first diameter.

19. The method of claim 18 wherein the ultrasonic probe has a tapered transition between the first region and the second region.

20. A method comprising:
moving an ultrasonic probe to a treatment site in a body such that the ultrasonic probe is in communication with a biological material;
producing a torsional vibration along the ultrasonic probe, the torsional vibration inducing a transverse vibration in a portion of the ultrasonic probe; and
applying a tension to the ultrasonic probe to tune the transverse vibration into coincidence with the torsional vibration.

21. The method of claim 20 wherein the portion of the ultrasonic probe in which the transverse vibration is induced supports the torsional vibration and the transverse vibration.

22. The method of claim 20 further comprising superimposing the torsional vibration and the transverse vibration along the portion of the ultrasonic probe in which the transverse vibration is induced.

23. The method of claim 20 further comprising segregating the torsional vibration and the transverse vibration along the ultrasonic probe.

24. The method of claim 20 wherein the torsional vibration is produced by a transducer coupled to the ultrasonic probe.

25. The method of claim 20 further comprising generating acoustic energy in a medium surrounding the ultrasonic probe through an interaction of a surface of the ultrasonic probe and the medium surrounding the ultrasonic probe resulting from the torsional vibration and the transverse vibration.

26. The method of claim 20 further comprising producing a plurality of nodes and a plurality of anti-nodes along at least the portion of the ultrasonic probe in which the transverse vibration is induced.

27. The method of claim 20 further comprising producing a plurality of transverse nodes and a plurality of transverse anti-nodes along at least the portion of the ultrasonic probe in which the transverse vibration is induced.

28. The method of claim 20 further comprising producing a rotation and counterrotation of the ultrasonic probe along at least the portion of the ultrasonic probe in which the transverse vibration is induced.

29. The method of claim 20 further comprising projecting the torsional vibration in a forward direction and a reverse direction about a plurality of nodes of the ultrasonic probe.

30. The method of claim 20 further comprising sweeping the ultrasonic probe along the treatment site.

31. The method of claim 20 further comprising moving the ultrasonic probe back and forth along the treatment site.

32. The method of claim 20 further comprising rotating the ultrasonic probe along the treatment site.

33. The method of claim 20 further comprising delivering ultrasonic energy to the ultrasonic probe in a frequency range from about 10 kHz to about 100 kHz.

34. The method of claim 20 further comprising determining a resonant frequency of the transducer and providing electrical energy to a transducer at the resonant frequency of the transducer.

35. The method of claim 20 further comprising providing the ultrasonic probe having a flexibility allowing the ultrasonic probe to support the torsional vibration and the transverse vibration.

36. The method of claim 20 wherein the portion in which the transverse vibration is induced extends along at least a portion of the longitudinal axis of the ultrasonic probe.

37. The method of claim 20 wherein the ultrasonic probe has a first region having a first diameter and a second region having a second diameter, wherein the second diameter is smaller than the first diameter.

38. The method of claim 37 wherein the ultrasonic probe has a tapered transition between the first region and the second region.

39. A method comprising:
moving an ultrasonic probe to a treatment site in a body such that the ultrasonic probe is in communication with a biological material;
producing a torsional vibration along the ultrasonic probe, the torsional vibration inducing a transverse vibration in a portion of the ultrasonic probe; and
bending the ultrasonic probe to tune the transverse vibration into coincidence with the torsional vibration.

40. The method of claim 39 wherein the portion of the ultrasonic probe in which the transverse vibration is induced supports the torsional vibration and the transverse vibration.

41. The method of claim 39 further comprising superimposing the torsional vibration and the transverse vibration along the portion of the ultrasonic probe in which the transverse vibration is induced.

42. The method of claim 39 further comprising segregating the torsional vibration and the transverse vibration along the ultrasonic probe.

43. The method of claim 39 wherein the torsional vibration is produced by a transducer coupled to the ultrasonic probe.

44. The method of claim 39 further comprising generating acoustic energy in a medium surrounding the ultrasonic probe through an interaction of a surface of the ultrasonic probe and the medium surrounding the ultrasonic probe resulting from the torsional vibration and the transverse vibration.

45. The method of claim 39 further comprising producing a plurality of nodes and a plurality of anti-nodes along at least the portion of the ultrasonic probe in which the transverse vibration is induced.

46. The method of claim 39 further comprising producing a plurality of transverse nodes and a plurality of transverse anti-nodes along at least the portion of the ultrasonic probe in which the transverse vibration is induced.

47. The method of claim 39 further comprising producing a rotation and counterrotation of the ultrasonic probe along at least the portion of the ultrasonic probe in which the transverse vibration is induced.

48. The method of claim 39 further comprising projecting the torsional vibration in a forward direction and a reverse direction about a plurality of nodes of the ultrasonic probe.

49. The method of claim 39 further comprising sweeping the ultrasonic probe along the treatment site.

50. The method of claim 39 further comprising moving the ultrasonic probe back and forth along the treatment site.

51. The method of claim 39 further comprising rotating the ultrasonic probe along the treatment site.

52. The method of claim 39 further comprising delivering ultrasonic energy to the ultrasonic probe in a frequency range from about 10 kHz to about 100 kHz.

53. The method of claim 39 further comprising determining a resonant frequency of the transducer and providing electrical energy to a transducer at the resonant frequency of the transducer.

54. The method of claim 39 further comprising providing the ultrasonic probe having a flexibility allowing the ultrasonic probe to support the torsional vibration and the transverse vibration.

55. The method of claim 39 wherein the portion in which the transverse vibration is induced extends along at least a portion of the longitudinal axis of the ultrasonic probe.

56. The method of claim 39 wherein the ultrasonic probe has a first region having a first diameter and a second region having a second diameter, wherein the second diameter is smaller than the first diameter.

57. The method of claim 56 wherein the ultrasonic probe has a tapered transition between the first region and the second region.

58. A method comprising:
   placing an ultrasonic probe in communication with a biological material in a body;
   activating an energy source to produce an electric signal that drives a transducer coupled to the ultrasonic probe to produce a torsional vibration along a portion of the flexible probe, the torsional vibration inducing a transverse vibration along the longitudinal axis of the flexible probe; and
   applying a tension to the flexible probe causing the transverse vibration to tune into coincidence with the torsional vibration.

59. The method of claim 58 further comprising superimposing the torsional vibration and the transverse vibration along the longitudinal axis of the ultrasonic probe.

60. The method of claim 58 further comprising segregating the torsional vibration and the transverse vibration along the longitudinal axis of the ultrasonic probe.

61. The method of claim 58 further comprising generating acoustic energy in a medium surrounding the ultrasonic probe through an interaction of a surface of the ultrasonic probe and the medium surrounding the ultrasonic probe resulting from the torsional vibration and a transverse vibration.

62. The method of claim 58 wherein the ultrasonic probe has a first region having a first diameter and a second region having a second diameter, wherein the second diameter is smaller than the first diameter.

63. The method of claim 62 wherein the ultrasonic probe has a tapered transition between the first region and the second region.

64. A method comprising:
   placing an ultrasonic probe in communication with a biological material in a body;
   activating an energy source to produce an electric signal that drives a transducer coupled to the ultrasonic probe to produce a torsional vibration along a portion of the flexible probe, the torsional vibration inducing a transverse vibration along the longitudinal axis of the flexible probe; and
   bending the flexible probe causing the transverse vibration to tune into coincidence with the torsional vibration.

65. The method of claim 64 further comprising superimposing the torsional vibration and the transverse vibration along the longitudinal axis of the ultrasonic probe.

66. The method of claim 64 further comprising segregating the torsional vibration and the transverse vibration along the longitudinal axis of the ultrasonic probe.

67. The method of claim 64 further comprising generating acoustic energy in a medium surrounding the ultrasonic probe through an interaction of a surface of the ultrasonic probe and the medium surrounding the ultrasonic probe resulting from the torsional vibration and a transverse vibration.

68. The method of claim 64 wherein the ultrasonic probe has a first region having a first diameter and a second region having a second diameter, wherein the second diameter is smaller than the first diameter.

69. The method of claim 68 wherein the ultrasonic probe has a tapered transition between the first region and the second region.

* * * * *

UNITED STATES PATENT AND TRADEMARK OFFICE
CERTIFICATE OF CORRECTION

PATENT NO. : 7,794,414 B2 Page 1 of 1
APPLICATION NO. : 10/774898
DATED : September 14, 2010
INVENTOR(S) : Robert A. Rabiner et al.

It is certified that error appears in the above-identified patent and that said Letters Patent is hereby corrected as shown below:

Col. 19, Ln. 45, Claim 58, Delete "flexible"
Insert --ultrasonic--.

Col. 19, Ln. 46, Claim 58, Delete "flexible"
Insert --ultrasonic--.

Col. 19, Ln. 48, Claim 58, Delete "flexible"
Insert --ultrasonic--.

Col. 20, Ln. 25, Claim 64, Delete "flexible"
Insert --ultrasonic--.

Col. 20, Ln. 26, Claim 64, Delete "flexible"
Insert --ultrasonic--.

Col. 20, Ln. 28, Claim 64, Delete "flexible"
Insert --ultrasonic--.

Signed and Sealed this

Ninth Day of November, 2010

David J. Kappos
*Director of the United States Patent and Trademark Office*